United States Patent
Chaplin et al.

(10) Patent No.: US 11,369,441 B2
(45) Date of Patent: Jun. 28, 2022

(54) DRIVE TRANSFER

(71) Applicant: CMR SURGICAL LIMITED, Cambridge (GB)

(72) Inventors: Ben Robert Chaplin, Cambridge (GB); James Oliver Grant, Cambridge (GB); Keith Marshall, Cambridge (GB); Nikki Priyam Su-Ling Phoolchund, Cambridge (GB); Thomas Bates Jackson, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 586 days.

(21) Appl. No.: 16/321,750

(22) PCT Filed: Jul. 27, 2017

(86) PCT No.: PCT/GB2017/052191
§ 371 (c)(1),
(2) Date: Jan. 29, 2019

(87) PCT Pub. No.: WO2018/020250
PCT Pub. Date: Feb. 1, 2018

(65) Prior Publication Data
US 2019/0151035 A1    May 23, 2019

(30) Foreign Application Priority Data
Jul. 29, 2016 (GB) ..................... 1613094

(51) Int. Cl.
*A61B 34/30*    (2016.01)
*A61B 46/10*    (2016.01)
*A61B 17/00*    (2006.01)
*A61B 17/29*    (2006.01)

(52) U.S. Cl.
CPC .............. *A61B 34/30* (2016.02); *A61B 46/10* (2016.02); *A61B 17/29* (2013.01);
(Continued)

(58) Field of Classification Search
CPC ... A61B 34/30; A61B 46/10; A61B 2034/305; A61B 2017/0023; A61B 2034/302; A61B 17/29; A61B 2017/00477; A61B 34/70
See application file for complete search history.

(56) References Cited

U.S. PATENT DOCUMENTS

2006/0161138 A1*  7/2006  Orban, III .............. A61B 34/35
606/1
2010/0170519 A1   7/2010  Romo et al.
(Continued)

FOREIGN PATENT DOCUMENTS

JP    2011516120 A    5/2011
JP    2014076361 A    5/2014
(Continued)

OTHER PUBLICATIONS

International Search Report and Written Opinion from corresponding PCT/GB2017/052191 dated Nov. 7, 2017.
(Continued)

*Primary Examiner* — Eugene T Wu
(74) *Attorney, Agent, or Firm* — Lando & Anastasi, LLP

(57) ABSTRACT

A drive transfer element for transferring drive between a surgical robot arm and a surgical instrument, the drive transfer element comprising a drive transfer element recess being releasably engageable with an interface protrusion; and a drive transfer element protrusion being releasably engageable with an interface recess; the drive transfer element protrusion comprising a cavity in communication with the drive transfer element recess so as to enable the interface protrusion engageable with the drive transfer element recess to project into the cavity.

16 Claims, 9 Drawing Sheets

(52) U.S. Cl.
CPC .............. *A61B 2017/0023* (2013.01); *A61B 2017/00477* (2013.01); *A61B 2034/302* (2016.02); *A61B 2034/305* (2016.02)

(56) References Cited

U.S. PATENT DOCUMENTS

| | | |
|---|---|---|
| 2011/0288573 A1 | 11/2011 | Yates et al. |
| 2012/0289973 A1 | 11/2012 | Prisco et al. |
| 2014/0296874 A1 | 10/2014 | Morgan et al. |
| 2014/0305988 A1 | 10/2014 | Boudreaux et al. |
| 2017/0027656 A1* | 2/2017 | Robert .................. F16C 1/12 |

FOREIGN PATENT DOCUMENTS

| | | |
|---|---|---|
| JP | 2018504285 A | 2/2018 |
| JP | 2018527056 A | 9/2018 |
| WO | 2016081286 A1 | 5/2016 |
| WO | 2016090459 A1 | 6/2016 |
| WO | 2016097861 A1 | 6/2016 |
| WO | 2017015167 A1 | 1/2017 |

OTHER PUBLICATIONS

United Kingdom Search Report from corresponding United Kingdom Application No. GB1613094.0 dated Jan. 27, 2017.
United Kingdom Search Report from corresponding United Kingdom Application No. GB2109891.8 dated Sep. 29, 2021.
English Translation of a Japanese Notification of Reasons for Refusal from corresponding Japanese Application No. 2019-504775 dated Jun. 1, 2021.

* cited by examiner

DRIVE TRANSFER

CROSS-REFERENCE TO RELATED APPLICATIONS

This application is a U.S. National Phase Application under 35 U.S.C. § 371 of International Application No. PCT/GB2017/052191, filed Jul. 27, 2017, which claims priority to United Kingdom Application No. 1613094.0 filed Jul. 29, 2016, which is hereby incorporated by reference in its entirety for all purposes.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between the base 201 and an articulation 203. The articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

A surgeon utilises many instruments during the course of a typical laparoscopy operation. For this reason, it is desirable for the instruments to be detachable from and attachable to the end of the robot arm with an ease and speed which enables instruments to be exchanged mid-operation. It is therefore desirable to minimise the time taken and maximise the ease with which one instrument is detached from a robot arm and a different instrument is attached.

The operating theatre is a sterile environment. The surgical robotic system must be sterile to the extent it is exposed to the patient. Surgical instruments are sterilised prior to use in an operation, however the robot arm is not sterilised prior to use. Instead, a sterile drape is placed over the whole of the surgical robot prior to the operation. In this way, the patient is not exposed to the non-sterile surgical robot arm. When exchanging instruments mid-operation, it is desirable for the sterile barrier to be maintained.

SUMMARY

According to an aspect of the present invention, there is provided a drive transfer element for transferring drive between a surgical robot arm and a surgical instrument, the drive transfer element comprising:
 a drive transfer element recess being releasably engageable with an interface protrusion; and
 a drive transfer element protrusion being releasably engageable with an interface recess;
 the drive transfer element protrusion comprising a cavity in communication with the drive transfer element recess so as to enable the interface protrusion engageable with the drive transfer element recess to project into the cavity.

Suitably the drive transfer element is drivable in a first direction to effect drive transfer, and the drive transfer element protrusion comprises a first outer wall facing the first direction for contacting a portion of the interface recess and the cavity comprises a first inner wall facing a second direction for contacting a portion of the interface protrusion.

Suitably the first outer wall and the first inner wall overlap one another in the first direction.

Suitably the second direction is opposite to the first direction.

Suitably the first outer wall overlaps the whole of the first inner wall in the first direction. Suitably the first outer wall and the first inner wall are parallel to one another.

Suitably the drive transfer element is drivable in a third direction to effect drive transfer and the drive transfer element protrusion comprises a second outer wall facing the third direction for contacting a portion of the interface recess and the cavity comprises a second inner wall facing a fourth direction for contacting a portion of the interface protrusion.

Suitably the second outer wall and the second inner wall overlap one another in the third direction.

Suitably the fourth direction is opposite to the third direction.

Suitably the second outer wall overlaps the whole of the second inner wall in the third direction. Suitably the second outer wall and the second inner wall are parallel to one another.

Suitably the third direction is opposite to the first direction.

Suitably the drive transfer element is arranged for reciprocating movement so as to transfer drive in two opposite directions. Suitably the drive transfer element is arranged for movement along a linear path. Suitably the overlap between the first outer wall and the first inner wall, and/or between the second outer wall and the second inner wall, permits drive to be transferred via a substantially compressive force. Suitably the compressive force is directed along the first direction and/or the third direction.

Suitably a wall of the drive transfer element recess is continuous with at least one of the first inner wall and the second inner wall. Suitably the wall of the drive transfer element recess is parallel with at least one of the first inner wall and the second inner wall.

Suitably the drive transfer element recess has a larger width than the cavity.

Suitably the drive transfer element recess has a larger width than the cavity in the first direction and/or the second direction. Suitably both the drive transfer element recess and the cavity are centrally located in the drive transfer element along the first direction and/or the second direction.

Suitably a first wall of the drive transfer element recess disposed towards the first direction is offset from the first inner wall, and a second wall of the drive transfer element recess disposed towards the third direction is offset from the second inner wall.

Suitably the first wall of the drive transfer element recess disposed towards the first direction is parallel but not co-planar with the first inner wall, and the second wall of the drive transfer element recess disposed towards the third direction is parallel but not co-planar with the second inner wall.

The drive transfer element may comprise a central portion which comprises the drive transfer element protrusion and the drive transfer element recess, and an extending portion which extends from the central portion, the drive transfer element recess being provided to a first side of the extending portion and the drive transfer element protrusion being provided to a second side of the extending portion. Suitably the extending portion permits the drive transfer element to be retained, for example slidably retained, relative to either or both of the robot arm and the instrument.

Suitably the drive transfer element is retained in an interface structure which interfaces between the robot arm and the instrument.

Suitably the drive transfer element, comprises a central portion which comprises the drive transfer element protrusion and the drive transfer element recess, and an extending portion which extends from the central portion, the drive transfer element recess being provided to a first side of the extending portion and the drive transfer element protrusion being provided to a second side of the extending portion, the drive transfer element permitting the interface protrusion engageable therewith to project from the first side through to the second side.

Suitably the communication between the drive transfer element recess and the cavity permits the interface protrusion engageable with the drive transfer element to project from the first side through to the second side.

Suitably at least a portion of the drive transfer element is symmetric about the first direction.

Suitably the central portion is symmetric about the first direction. Suitably the central portion and the extending portion are symmetric about the first direction.

According to an aspect of the present invention, there is provided an interface structure for detachably interfacing a surgical robot arm to a surgical instrument, the interface structure comprising:
 a main body; and
 a drive transfer element as described above, the drive transfer element being movable relative to the main body so as to enable transfer of drive between the surgical robot arm and the surgical instrument.

Suitably the main body comprises an aperture within which the drive transfer element is movable.

Suitably the main body comprises a retention feature for retaining the drive transfer element so that the drive transfer element is movable within the aperture.

Suitably the retention feature comprises a lip or channel along at least a portion of the length of the aperture within which at least a portion of the extending portion of the drive transfer element is receivable and along which the received portion of the drive transfer element is movable. Suitably the received portion of the drive transfer element is slidably movable along the lip or channel.

According to an aspect of the present invention, there is provided a surgical robot arm comprising:
 a drive assembly towards a distal end of the arm which is engageable with a surgical instrument having an articulation for articulating an end effector, the drive assembly comprising a drive assembly interface element; and
 an interface structure as described above;
the drive assembly interface element being engageable with the drive transfer element so as to transfer drive between the robot arm and the instrument.

Suitably the drive assembly interface element comprises the interface protrusion.

Suitably the drive assembly interface element comprises a strengthening or stiffening portion. The strengthening portion is suitably for resisting bending of the drive assembly interface element.

Suitably the strengthening portion resists bending of the drive assembly interface element as the drive assembly interface element is driven. Suitably the strengthening portion comprises one or more of a buttress portion, a strut, or other abutment or fillet, or a gusset. Suitably the strengthening portion is disposed towards a distal end of the drive assembly interface element from the protrusion which is engageable with the drive transfer element.

According to an aspect of the present invention there is provided a drive assembly locatable on a distal end of a robot arm for transferring drive between the robot arm and an instrument attachable to the robot arm, the drive assembly comprising a drive assembly interface and a drive assembly interface element which is movable relative to the drive assembly interface, the drive assembly interface element comprising a strengthening portion for resisting bending of the drive assembly interface element. Suitably the robot arm is a surgical robot arm. Suitably the instrument is a surgical instrument. Suitably the drive assembly interface element comprises the interface protrusion.

According to an aspect of the present invention there is provided a surgical system comprising the surgical robot arm as described above and a surgical instrument, the surgical instrument comprising an instrument interface element being engageable with the drive transfer element so as to transfer drive between the robot arm and the instrument.

Suitably the instrument interface element comprises the interface recess.

According to an aspect of the present invention there is provided a drive assembly locatable at or towards a distal end of a robot arm, the drive assembly comprising a drive assembly interface which is engageable with an instrument comprising an end effector so as to transfer drive between the drive assembly and the instrument, the drive assembly interface comprising a drive assembly interface element movable relative to the drive assembly interface and engageable with a corresponding instrument interface element provided on the instrument; the drive assembly being configured to drive the drive assembly interface element to an interfacing position for engaging with the instrument interface element.

Suitably the instrument is a surgical instrument. Suitably the robot arm is as a surgical robot arm.

Suitably the drive assembly interface element is movable relative to the drive assembly interface to transfer drive. Suitably the drive assembly interface element is movable along a path, such as a linear path. Suitably the interfacing position is located at the centre of travel of the path. Suitably the interfacing position is located towards or at one end of the path.

Suitably the drive assembly comprises a sensor for sensing the position of the drive assembly interface element. Suitably the sensor senses when the drive assembly interface element passes a threshold position. Suitably the sensor comprises at least one of a magnetic sensor, a light sensor, a capacitive sensor, an inductive sensor, an acoustic sensor and a microswitch.

Suitably the drive assembly interface comprises a plurality of drive assembly interface elements, each movable relative to the drive assembly interface along a respective path, and drivable to a respective interfacing position. Suitably at least two drive assembly interface elements are aligned with one another when in their respective interfacing positions. Suitably each drive assembly interface element has associated therewith a respective sensor for sensing the position of that drive assembly interface element.

Suitably the sensor is configured to determine whether the drive assembly interface element is in its interfacing position. Suitably each sensor is configured to determine whether the respective drive assembly interface element is in its respective interfacing position.

According to an aspect of the present invention there is provided a method of engaging an instrument comprising an instrument interface element with a drive assembly comprising a drive assembly interface element, the method comprising:

driving the drive assembly interface element to an interfacing position; and engaging the instrument with the drive assembly by engaging the instrument interface element with the drive assembly interface element when it is in the interfacing position.

Suitably the method comprises sensing the position of the drive assembly interface element with a sensor, determining whether the drive assembly interface element is in the interfacing position in dependence on an output of the sensor, and engaging the instrument with the drive assembly when it is determined that the drive assembly interface element is in the interfacing position.

Any one or more features of any aspect above may be combined with any one or more features of that aspect and/or any other aspect above. These have not been written out in full here for the sake of brevity.

BRIEF DESCRIPTION OF THE FIGURES

The present invention will now be described by way of example with reference to the accompanying drawings. In the drawings:

FIG. 7b illustrates the other side of the interface structure of FIG. 7a;

FIG. 8 illustrates an axial cross-sectional view of an instrument interfaced with a drive assembly via the interface structure of FIG. 7a;

FIG. 9 illustrates a side cross-sectional view of an instrument interfaced with a drive assembly via the interface structure of FIG. 7a;

FIG. 10b schematically illustrates a plan view of the alternative interface structure shown in FIG. 10a.

DETAILED DESCRIPTION

Figure 3:
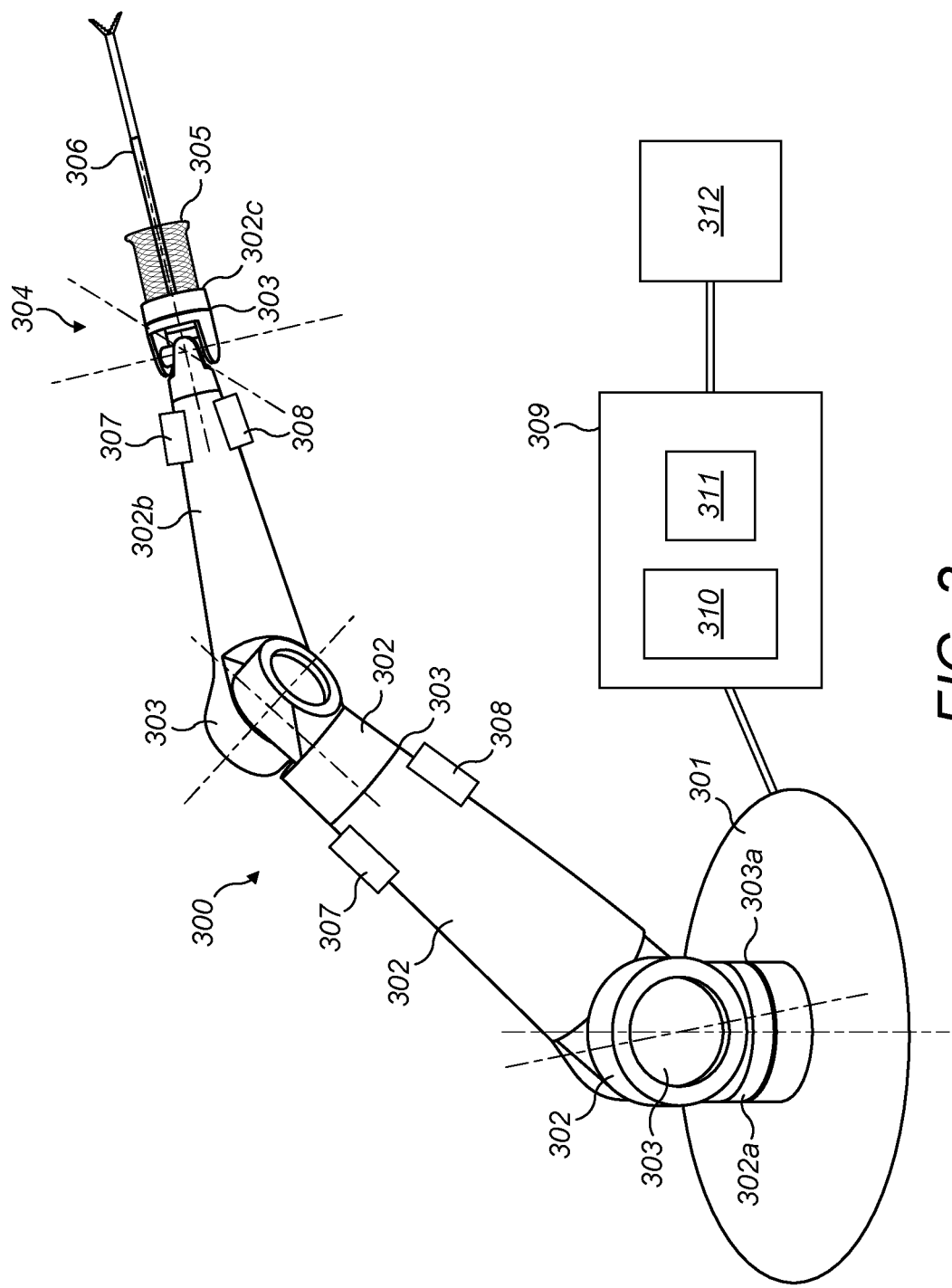
FIG. 3 illustrates a surgical robot.

FIG. 3 illustrates a surgical robot having an arm 300 which extends from a base 301. The arm comprises a number of rigid limbs 302. The limbs are coupled by revolute joints 303. The most proximal limb 302a is coupled to the base by a proximal joint 303a. It and the other limbs are coupled in series by further ones of the joints 303. Suitably, a wrist 304 is made up of four individual revolute joints. The wrist 304 couples one limb (302b) to the most distal limb (302c) of the arm. The most distal limb 302c carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Figure 1:
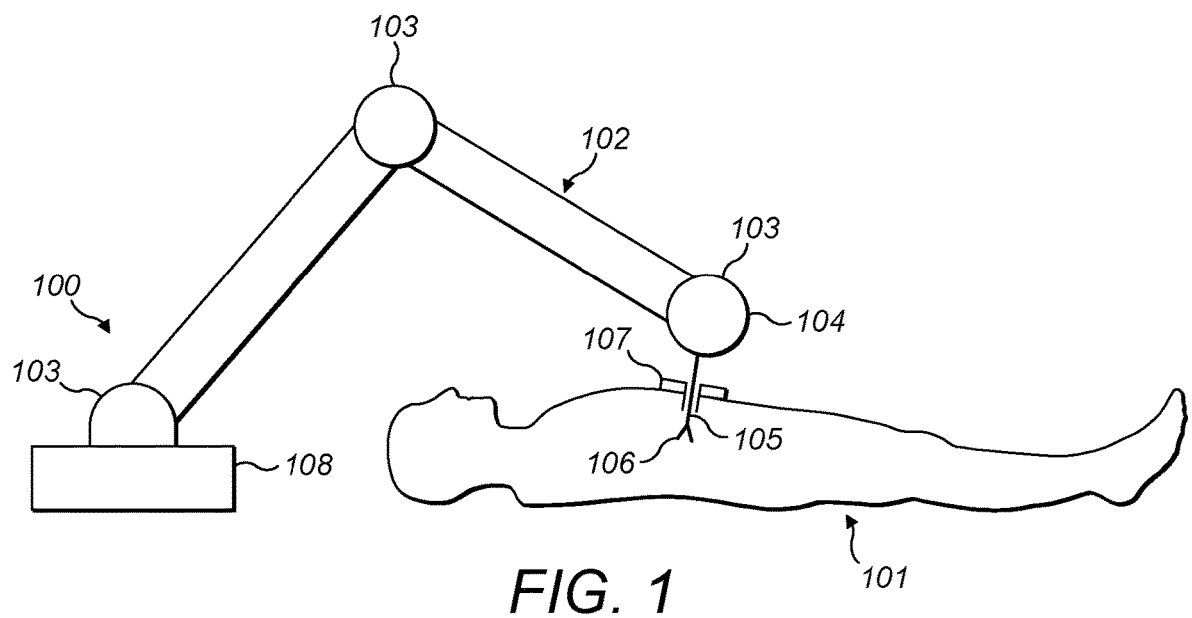
FIG. 1 illustrates a surgical robot performing a surgical procedure.
Figure 2:
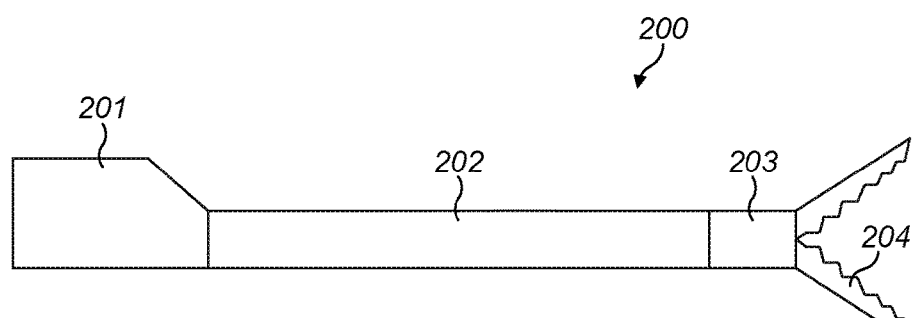
FIG. 2 illustrates a known surgical instrument.

The arm terminates in the attachment 305 for interfacing with the instrument 306. Suitably, the instrument 306 takes the form described with respect to FIG. 2. The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable to and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed within the robot arm. The controllers are connected via a communication bus to a control unit 309. The control unit 309 comprises a processor 310 and a memory 311. The memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in the memory 311 is configured to respond to those inputs and cause the joints of the arm and instrument to move accordingly, in compliance with a predetermined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Figure 4:
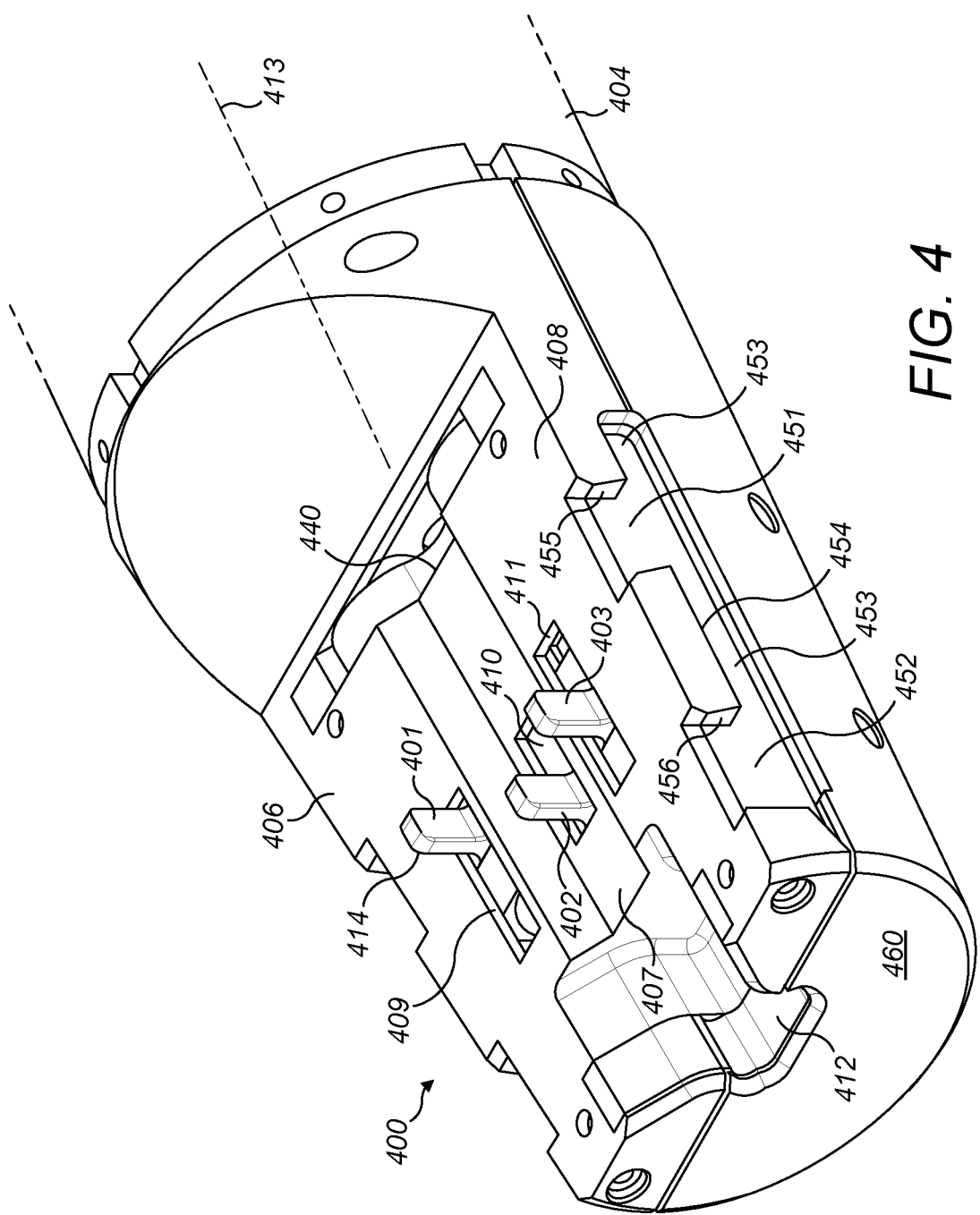
FIG. 4 illustrates a drive assembly interface of a surgical robot arm.
Figure 5:
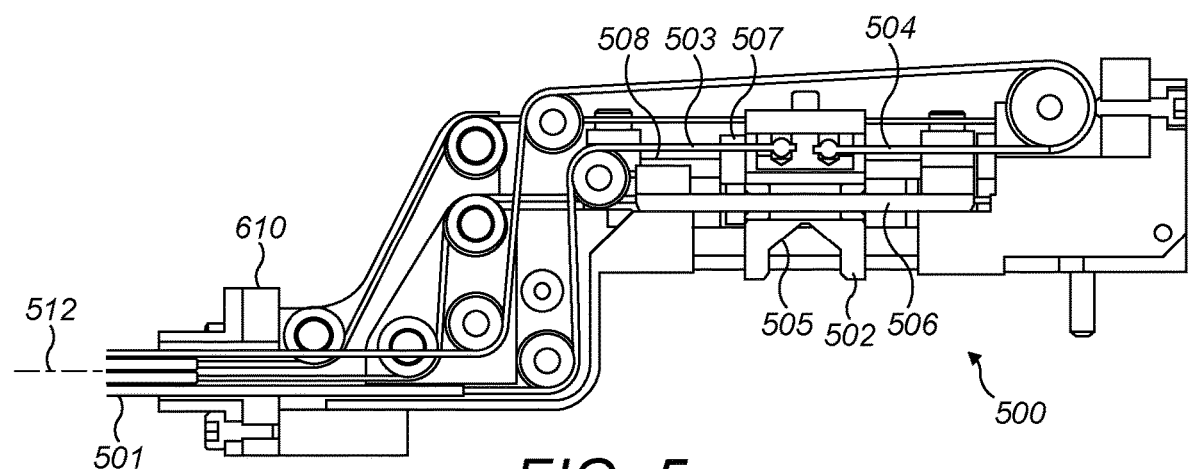
FIG. 5 illustrates an instrument interface of a surgical instrument.

FIGS. 4 and 5 illustrate an exemplary mechanical interconnection of the drive assembly interface and the instrument interface in order to transfer drive from the robot arm to the instrument. FIG. 4 illustrates an exemplary drive assembly interface 400 at the end of a robot arm 404. The drive assembly interface 400 comprises a plurality of drive assembly interface elements 401, 402, 403. The drive assembly interface elements protrude from surfaces 406, 407, 408 on the drive assembly interface 400. The protrusion of the drive assembly interface elements from the drive assembly interface 400 permits engagement of the drive assembly interface elements with corresponding instrument interface elements, as described below. The protrusions are in the form of fins in the illustrated example. In other implementations, other types of protrusion can be provided. The drive assembly interface elements suitably comprise a stiff material, such as a metal. Suitably the protrusion is formed from a stiff material, such as a metal. Preferably the drive assembly interface element is formed from a stiff material, such as a metal.

The protrusions (the fins in the illustrated example) comprise a chamfer 414 at their distal ends. The chamfer provides for ease of engagement of the protrusions in corresponding recesses, as described below. In other examples the distal ends of the protrusions can be provided with a rounded corner. The edges of the chamfered portions can be rounded.

The fins extend through the surfaces 406, 407, 408. The portions of the fins that protrude from the surfaces are perpendicular to the plane of the surfaces. In other examples the fins can protrude in a direction that is within a range of 10 degrees from perpendicular. Preferably the direction in which the fins extend is within a range of 5 degrees or within a range of 2 degrees from perpendicular.

FIG. 4 illustrates three drive assembly interface elements. In other examples, there may be greater than or fewer than three drive assembly interface elements. The drive assembly interface elements 401, 402, 403 are movable within the drive assembly interface 400 along linear paths 409, 410, 411. The paths can be parallel with one another. Suitably at least two of the paths are parallel. The paths need not be precisely parallel with one another. There may be some tolerance in how closely aligned the paths need to be. For example, the paths may be within 10 degrees of each other. The paths may extend in respective directions within a 10 degree range. Preferably the paths are within 5 degrees of each other, or within 2 degrees or 1 degree of each other. The paths may extend in respective directions within a 5 degree range, or preferably a 2 degree or 1 degree range.

Aligning the paths in this manner can assist in providing corresponding mechanisms more compactly. For instance, the mechanisms can be arranged to move alongside one another, permitting the mechanisms to be arranged more closely together.

In the illustrated example, the linear paths 409, 410, 411 are disposed on two parallel planes. The central linear path 410 is disposed on a plane 407 set into the drive assembly interface 400 compared to that in which the outer two linear paths 409, 411 are disposed. This arrangement permits a more compact interface between the drive assembly interface 400 and an instrument interface 500, as will be described below.

In other implementations, the three linear paths 409, 410, 411 can be disposed on the same plane, or all on different planes. In another example, the outer two linear paths 409, 411 are disposed on a plane set into the drive assembly interface 400 compared to that in which the central linear path 410 is disposed. In implementations utilising differing numbers of drive assembly interface elements, different configurations of planes on which the paths are disposed are possible.

The drive assembly interface 400 comprises a recessed portion 412 for receiving a portion of the instrument. This arrangement can permit a more compact configuration when the instrument is mounted onto the robot arm.

Referring now to FIG. 5, the shaft 501 of the instrument terminates in the instrument interface 500. The instrument interface 500 comprises a plurality of instrument interface elements (one of which is shown at 502 in FIG. 5; these can more clearly be seen in FIG. 6 at 502, 507, 509). The instrument interface elements suitably comprise a stiff material, such as a metal. Suitably the instrument interface element is formed from a stiff material, such as a metal. Pairs of driving elements (one such pair is shown at 503, 504) extend into the instrument interface 500 from the end of the shaft 501. Each pair of driving elements terminates in one of the instrument interface elements. In the example shown in FIG. 5, the driving element pair 503, 504 terminates in instrument interface element 502; likewise, other driving element pairs terminate in corresponding instrument interface elements.

In the illustrated example there are three driving element pairs that terminate in three instrument interface elements. In other examples, there may be greater than or fewer than three instrument interface elements. There may be greater than or fewer than three driving element pairs. In FIG. 5 there is a one-to-one relationship between instrument interface elements and driving element pairs. In other examples, there may be any other coupling relationship between the instrument interface elements and driving element pairs. For example, a single instrument interface element may drive more than one pair of driving elements. In another example, more than one instrument interface element may drive a single pair of driving elements.

Each instrument interface element 502, 507, 509 comprises a recess, or cup 505, which is the portion of the instrument interface element engageable with the drive assembly interface element.

The instrument interface elements are displaceable within the instrument interface. In the example shown, the instrument interface elements are slideable along rails. Instrument interface element 502 is slideable along rail 506. Instrument interface element 507 is slideable along rail 508. Instrument interface element 509 is slideable along rail 510. Each instrument interface element is displaceable along a direction parallel to the direction of elongation of the pair of driving elements which that instrument interface element holds captive. Each instrument interface element is displaceable in a direction parallel to the longitudinal axis 512 of the instrument shaft 501. When the instrument interface element moves along its respective rail, it causes a corresponding movement to the driving element pair secured to it. Thus, moving an instrument interface element drives motion of a driving element pair and hence motion of a joint of the instrument.

Drive assembly interface 400 mates with instrument interface 500. The instrument interface 500 comprises structure for receiving the drive assembly interface elements 401, 402, 403. Specifically, the instrument interface elements 507, 502, 509 receive drive assembly interface elements 401, 402, 403. In the example shown, each instrument interface element comprises a socket or cup 505 for receiving the fin of the corresponding drive assembly interface element. The socket 505 of one instrument interface element 502 receives a fin of the corresponding drive assembly interface element 402. Similarly, sockets of the other instrument interface elements receive fins of the other drive assembly interface elements.

Figure 8:
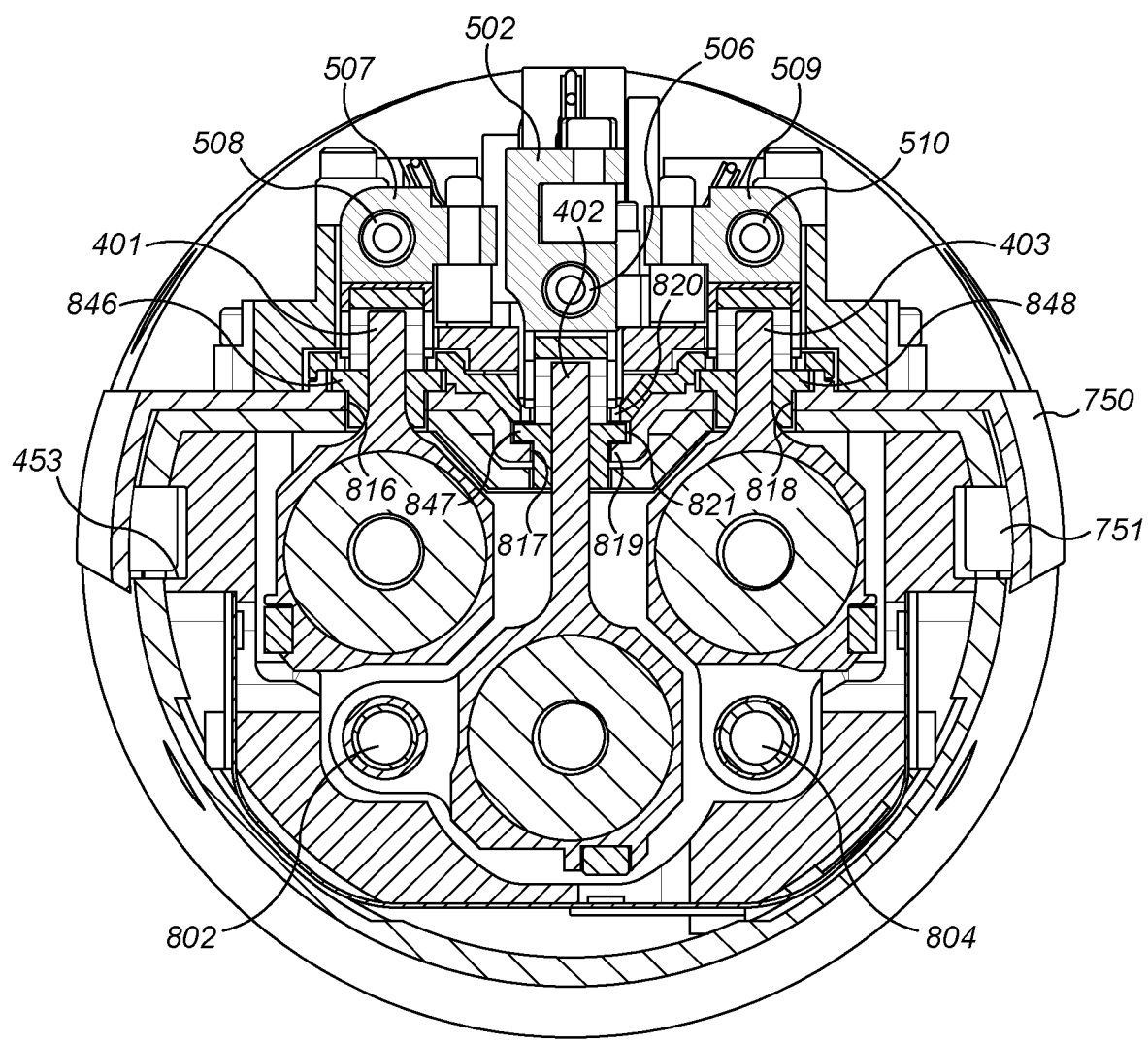

Each drive assembly interface element is displaceable within the drive assembly. This displacement is driven. For example, the displacement may be driven by a motor and lead screw arrangement. In the example shown, the drive assembly interface elements are slideable along drive rails 802, 804. Each drive assembly interface element is coupled to one drive rail. Referring to FIG. 8, the right-hand drive assembly interface element 403 is coupled to a right-hand drive rail 804. The central drive assembly interface element 402 is coupled to a left-hand drive rail 802. Whilst not shown, the left-hand drive assembly interface element 401 is coupled to the left-hand drive rail 802. In other configurations, the central drive assembly interface element is coupled instead to the right-hand drive rail 804, or to both of the left-hand drive rail 802 and the right-hand drive rail 804.

Coupling the central drive assembly interface element 402 to both the left-hand drive rail and to the right-hand drive rail assists in stabilising the central drive assembly interface element. For the arrangement illustrated in FIG. 8, where the central drive assembly interface element is elongate in the vertical direction of FIG. 8, this can reduce bending or rotation of the central drive assembly interface element as it moves and drives the corresponding drive transfer element.

Each drive assembly interface element is displaceable along a direction parallel to the longitudinal axis 413 of the terminal link of the robot arm. When the drive assembly interface element moves along its rail, it causes a corresponding movement to the instrument interface element to which it is engaged. Thus, driving motion of a drive assembly interface element drives motion of an instrument interface element which drives articulation of the end effector of the instrument.

The portions of the fins that protrude from the surfaces comprise front and rear faces aligned in the directions of movement of the drive assembly interface elements. Here, front and rear refer to movement in one direction, when the front face will face the direction of movement and the rear face will face away from the direction of movement. When the drive assembly interface element moves in the opposite direction, the front face will face away from the direction of movement and the rear face will face the direction of movement.

The front and rear faces of the drive assembly interface elements are transverse to the direction in which the drive assembly interface elements are driveably movable. The front and rear faces of the drive assembly interface elements are parallel to the direction in which the fins protrude from the surfaces. The front and rear faces need not be exactly parallel to this direction, but are preferably within a range of 10 degrees, or within a range of 5 degrees, or more preferably within a range of 2 degrees of this direction.

The socket 505 comprises an interior face that is transverse to the direction in which the instrument interface elements are movable. The interior face need not be exactly transverse to this direction, but is preferably within a range of 10 degrees, or within a range of 5 degrees, or more preferably within a range of 2 degrees of being transverse to this direction.

In the illustrated example the interior face of the instrument interface elements and the front and rear faces of the drive assembly interface elements are parallel to one another. This can assist in the transferral of drive between the elements.

In FIGS. 4 and 5 there is a one-to-one relationship between instrument interface elements and drive assembly interface elements. In other examples, there may be any other coupling relationship between the instrument interface elements and drive assembly interface elements. For example, a single drive assembly interface element may drive more than one instrument interface element. In another example, more than one drive assembly interface element may drive a single instrument interface element.

Figure 6:
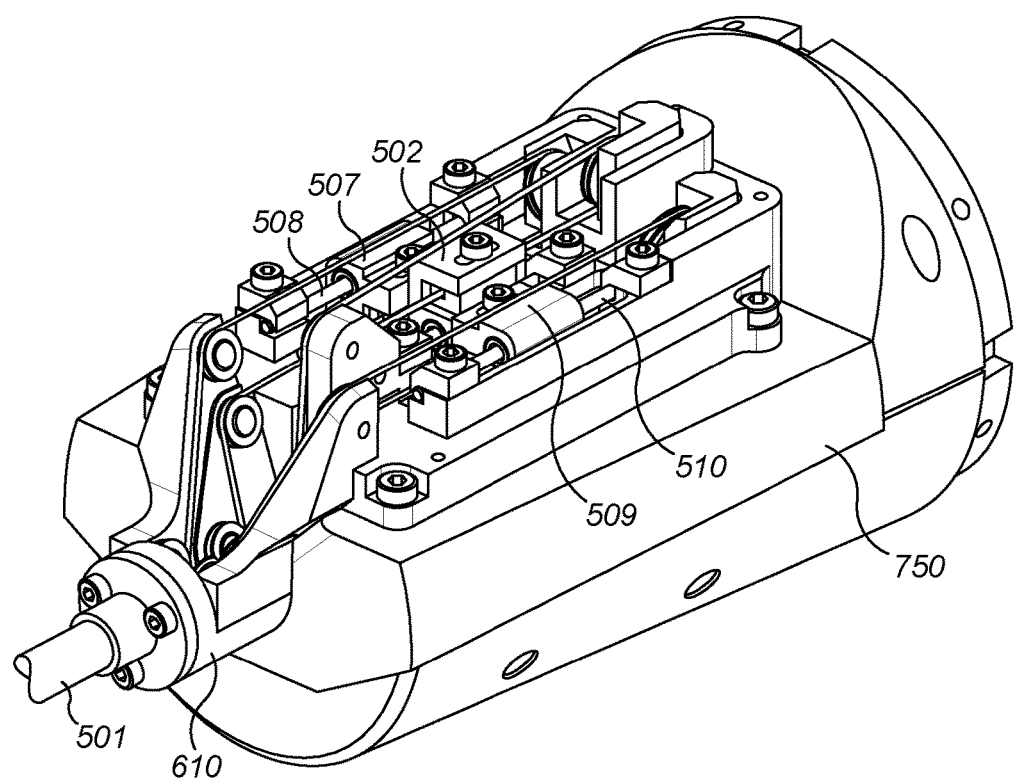
FIG. 6 illustrates the drive assembly interface of a robot arm with attached instrument.

FIG. 6 illustrates the instrument being placed into engagement with the robot arm. When drive assembly interface element 401 is held captive by instrument interface element 507, drive assembly interface element 402 is held captive by instrument interface element 502, and drive assembly interface element 403 is held captive by instrument interface element 509, the instrument interface elements and the drive assembly interface elements are all displaceable in the same direction. This direction is parallel to both the longitudinal axis 413 of the terminal link of the robot arm 404 and the longitudinal axis 512 of the instrument shaft 501.

During an operation or surgical procedure, the surgical robot is shrouded in a sterile drape to provide a sterile barrier between the non-sterile surgical robot and the sterile operating environment. The surgical instrument is sterilised before being attached to the surgical robot. The sterile drape is typically constructed of a plastic sheet, for example made of polyester, polypropylene, polyethylene or polytetrafluoroethylene (PTFE). Suitably, the drape is flexible and/or deformable.

Figure 7A:
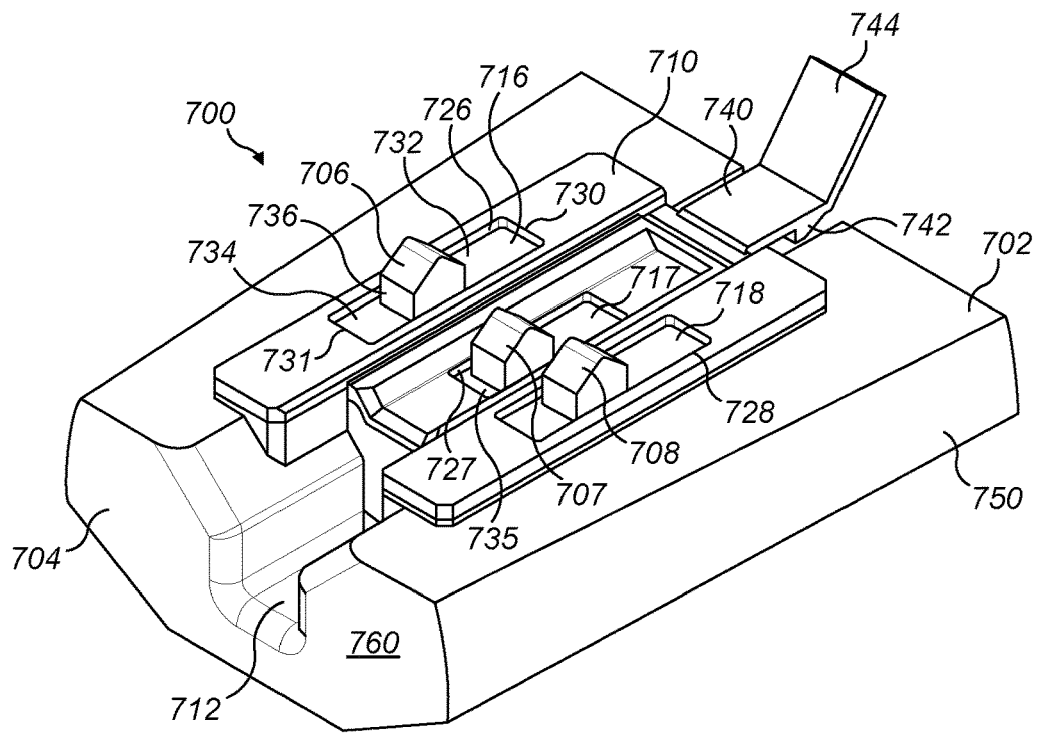
FIG. 7a illustrates one side of an interface structure.
Figure 7B:
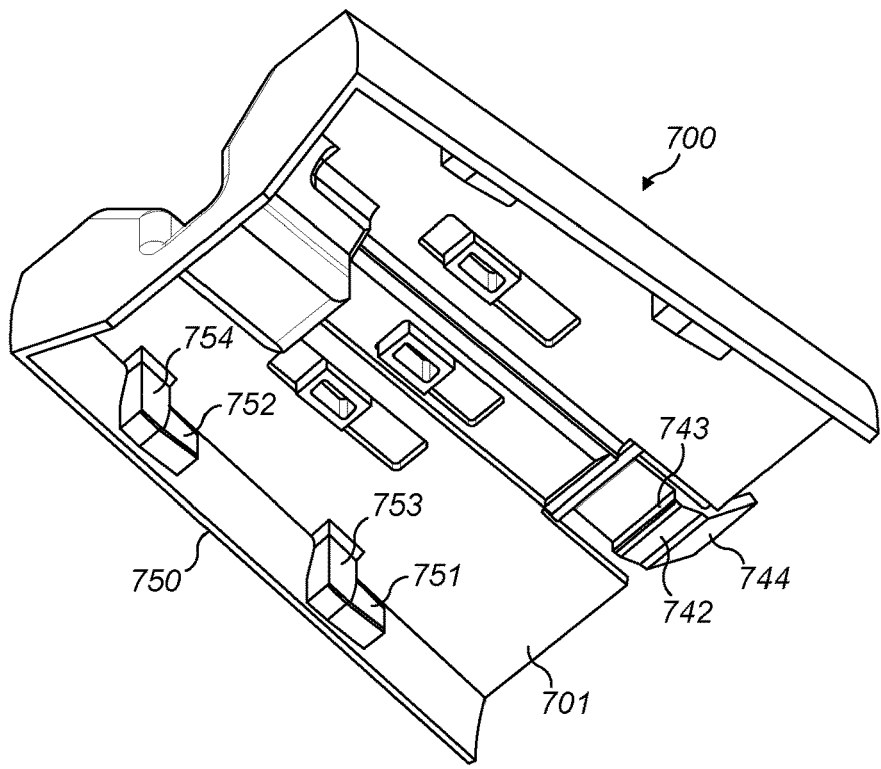

The sterile drape does not pass directly between the drive assembly interface 400 and the instrument interface 500. The drape comprises an interface structure 700 for interfacing between the drive assembly interface 400 and the instrument interface 500. FIGS. 7a and 7b show an exemplary interface structure 700 in isolation. The interface structure 700 is also shown in FIG. 6 attached to the drive assembly interface 400 and to the instrument interface 500. The interface structure 700 may be integrally formed with the drape. Alternatively, the interface structure 700 may be formed separately from the drape and subsequently attached to the drape. Either way, the interface structure 700 is sterile.

One side 701 of the interface structure 700 directly contacts the drive assembly interface. The other side 702 of the interface structure 700 directly contacts the instrument interface. Thus, the interface structure 700 prevents the non-sterile drive assembly interface from directly touching the sterile instrument interface and hence maintains the sterile barrier between the two components.

The interface structure 700 comprises a main body 704 and drive transfer elements 706, 707, 708. The drive transfer elements are movable relative to the main body. Conveniently, when the interface structure 700 is attached to the surgical robot arm, the main body 704 lies parallel to the surface(s) of the drive assembly interface 400. Suitably in this attached configuration, the main body 704 is aligned with the drive assembly interface.

The main body 704 comprises a first side 701 which faces the robot arm when the instrument is attached to the robot arm. Specifically, the first side 701 faces the drive assembly 400. The main body 704 comprises a second side 702 opposite to the first side. The second side 702 faces the instrument when the instrument is attached to the robot arm. Specifically, the second side 702 faces the instrument interface 500. Suitably both the first side 701 and the second side 702 are substantially flat. The first side and the second side need not be completely flat. Being substantially flat, or flat over at least a portion of its surface (for example over at least 10% of its surface, over at least 20% of its surface, over at least 30% of its surface, preferably over at least 40% of its surface or more preferably over at least 50% of its surface) permits the interface structure 700 to be compactly sandwiched between the instrument and the robot arm when the instrument is attached to the robot arm.

Being flat can include having flat portions in different planes. For example, as illustrated in FIG. 4, the drive assembly interface 400 can have portions which are flat, but disposed generally over two planes, as described above. Suitably the interface structure 700 is configured to correspond to the general surface features of the drive assembly interface so as to compactly engage therewith, reducing or minimising gaps or space between the interface structure and the drive assembly interface.

The main body 704 comprises an aperture. In the interface structure 700 illustrated in FIGS. 7a, 7b and 8, an aperture is located generally central to the main body 704, though it need not be located in this position. In the illustrated example, the main body 704 comprises three apertures: a first aperture 816, a second aperture 817 and a third aperture 818 (as can be seen in FIG. 8). The apertures 816, 817, 818 provide for communication between the first side 701 and the second side 702 though the main body 704.

A cover 710 is provided which covers a portion of the main body 704. The cover covers the part of the main body that comprises the apertures. In the illustrated implementation, the cover 710 is located on the second side 702 of the main body 704. In other examples, the cover can be located on the first side 701 of the main body, or covers can be located on both sides of the main body. The cover 710 is attached to the main body 704. Suitably the cover 710 is fixed to the main body 704. The cover can be attached to the main body by adhesive, or by any other convenient means or method of attachment.

The cover 710 comprises further apertures, or slots. In the illustrated example, the cover 710 comprises a first slot 726, a second slot 727 and a third slot 728. The slots communicate with the apertures in the main body 704. The first slot 726 is aligned with the first aperture 816; the second slot 727 is aligned with the second aperture 817; the third slot 728 is aligned with the third aperture 818. Thus the slots in the cover 710 provide fluid flow paths between the first side and the second side 702 of the main body.

The apertures 816, 817, 818 in the main body 704 define paths along which the drive transfer elements are movable. In the example illustrated in FIGS. 7a and 7b, the paths are linear paths. The first aperture 816 defines a first path; the second aperture 817 defines a second path; the third aperture 818 defines a third path.

The main body 704 and the cover 710 define therebetween channels along which drive transfer elements are movable. Suitably the drive transfer elements are slideable within the channels.

Referring to FIG. 8, a lip 819 adjacent an aperture in the main body 704 and a corresponding lip 820 adjacent an aperture in the cover 710 define a channel 821 between the lips. The main body 704 and the cover 710 define two channels per aperture, one to either side of the aperture. The channels extend along the length of the apertures.

As mentioned above, the interface structure 700 comprises drive transfer elements. In the example illustrated in FIGS. 7a and 7b, the interface structure comprises three drive transfer elements: a first drive transfer element 706, a second drive transfer element 707 and a third drive transfer element 708. The first drive transfer element 706 is slidably received in the first slot 726. The second drive transfer element 707 is slidably received in the second slot 727. The third drive transfer element 708 is slidably received in the third slot 728. Each drive transfer element is slidably movable along its respective slot.

The drive transfer elements comprise a central portion and an extending portion which extends away from the central portion. With reference to the first drive transfer element 706, the central portion 736 comprises a protrusion. The extending portion 716 comprises a flat plate that extends from the central portion 736. The extending portion 716 is elongate in two opposite directions which, when the first drive transfer element 706 is located in the first slot 726, are aligned with the directions in which the first slot 726 extends. In directions transverse to these directions, i.e. in directions transverse to the extent of the slots, the first drive transfer element comprises a first lip 846 as can be seen from FIG. 8. The first lip 846 is receivable into channels to either side of the first aperture 816. Similarly, a second lip 847 on the second drive transfer element 707 is receivable into channels to either side of the second aperture 817. A third lip 848 is receivable into channels to either side of the third aperture 818. Suitably the drive transfer elements are rigid.

The drive transfer elements extending along the slots restricts the fluid flow path through the apertures. The drive transfer elements extending into the channels adjacent the apertures restricts the fluid flow path through the apertures. In this way the drive transfer elements restrict the fluid flow path around the drive transfer elements.

Suitably the inter-engagement between the drive transfer elements 706, 707, 708 and the main body 704 is such as to restrict the fluid flow path between the drive transfer elements and the main body. This inter-engagement is, for example, by a portion of the drive transfer elements being retained adjacent the main body, such as by being retained in the slots, or by being retained in the channels.

The first slot 726 comprises a first end 730 and a second end 731 opposite the first end, along the length of the first slot. The extending portion 716 of the first drive transfer element 706 comprises a first extension 732 and a second extension 734. The length of the first extension 732 from the central portion 736 of the first drive transfer element 706 is L1. The length of the second extension 734 from the central portion 736 of the first drive transfer element 706 is L2.

At the furthest extent of movement of the first drive transfer element 706 towards the second end 731 of the first slot 726, the distance between the central portion 736 and the first end 730 is D1. At the furthest extent of movement of the first drive transfer element 706 towards the first end 730 of the first slot 726, the distance between the central portion 736 and the second end 731 is D2.

The length of the first extension L1 is at least the same as the distance D1. Suitably L1 is greater than D1, for example to provide an overlap between the first extension and the main body and/or between the first extension and the cover. The length of the second extension L2 is at least the same as the distance D2. Suitably L2 is greater than D2, for example to provide an overlap between the first extension and the main body and/or between the first extension and the cover. In this way, the extending portion 716 (comprising the first extension 732 and the second extension 734) covers the aperture. In other words, it covers the space between the central portion and the ends of the slots. Providing the extension portions 732, 734 to be the same length as, or greater than, the potential gap means that the gap will remain covered throughout the extent of movement of the drive transfer element within the slot.

The second drive transfer element 707 and the third drive transfer element 708 are similarly configured. For example, the second drive transfer element 707 comprises a third extension 735. Thus each aperture or slot remains covered throughout the whole extent of movement of the respective drive transfer element.

Referring to FIGS. 7a and 7b, the slots are not all of equal length. The second slot 727 is shorter than the first slot 726 and the third slot 728. The slots need not be sized in this particular way. Each slot can be sized as desired to account for or permit the required movement of the respective drive transfer element. In this example the central drive assembly interface element 402 is configured to move along a shorter linear path 410 than the linear paths 409, 411 along which the left-hand drive assembly interface element 401 and the right-hand drive assembly interface element 403 are configured to move. Correspondingly the first slot 726 and the third slot 728 are longer than the second slot 727. In the illustrated example the first drive transfer element and the third drive transfer element have a relative movement with respect to the main body of ±5.1 mm (i.e. 10.2 mm from one end to the other). The second drive transfer element has a relative movement with respect to the main body of ±3 mm (i.e. 6 mm from one end to the other). The relative movements need not be the same as these. In some examples the relative movement of the first and third drive transfer elements is longer or shorter than this. The relative movement of the second drive transfer element can be longer or shorter than this. The ratio of relative movements need not be this ratio, but could be greater or less than this ratio.

Figure 9:
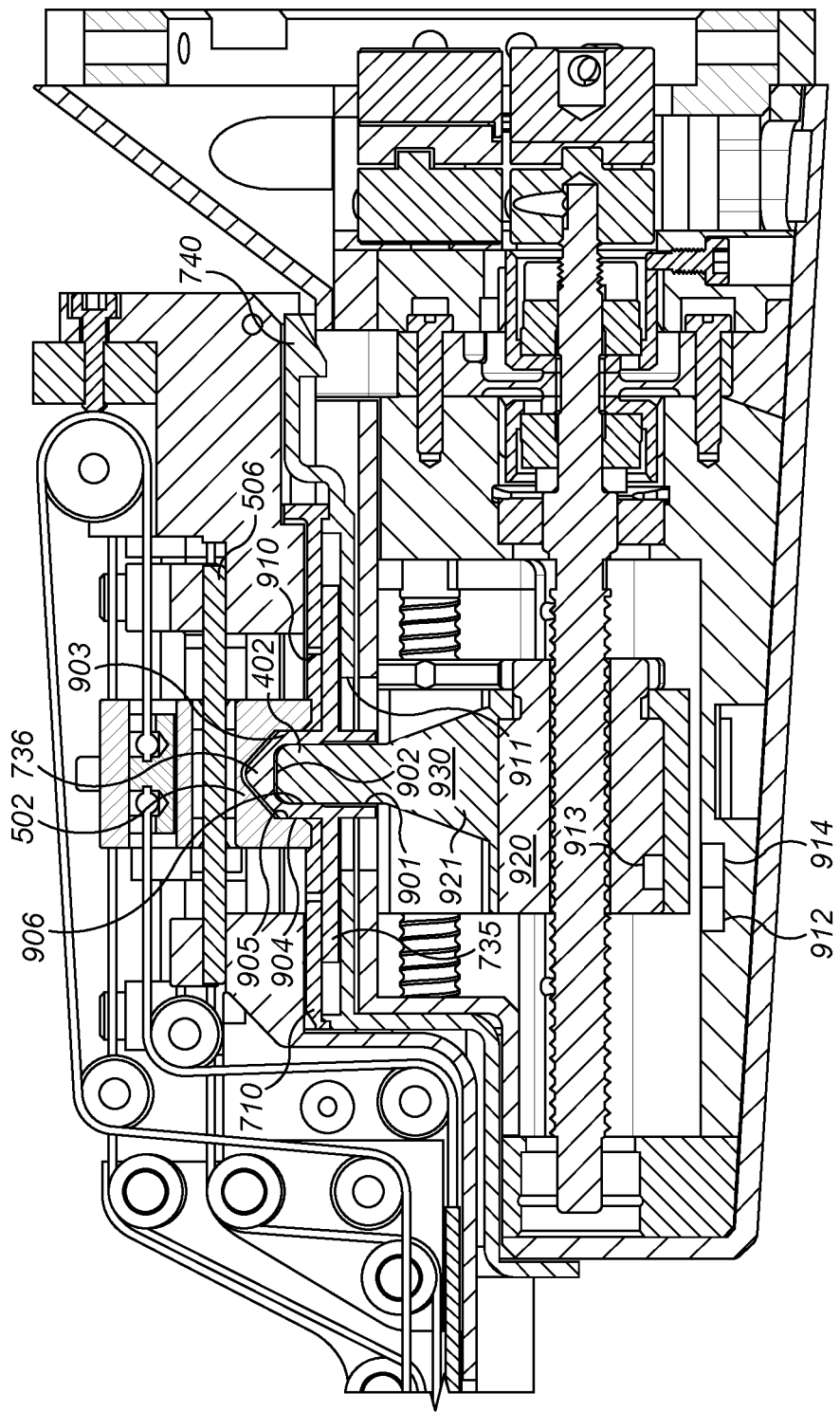

As can be seen from FIG. 9, the ends 910 of the slot in the cover are further apart than the ends 911 of the aperture in the main body. The slot in the cover is longer than the respective aperture in the main body. This additional length permits the socket 502 to protrude at least partially within the slot in the cover without reducing the travel of the drive transfer element within the aperture. Suitably the additional length of the slot compared to the aperture is at least equal to the width of that portion of the socket disposed between the drive transfer element and the end 910 of the slot. Suitably the additional length of the slot compared to the aperture is at least equal to twice the width of that portion of the socket disposed between the drive transfer element and the end 910 of the slot, so as to avoid reducing the travel of the drive transfer element within the aperture at either end of the range of movement.

The protrusion of the socket 502 at least partially within the slot in the cover permits better coupling between the socket and the drive transfer element. The protrusion of the socket at least partially within the slot in the cover permits better coupling between the socket and the fin. The coupling is improved by providing a greater overlap between the socket and the fin in the direction of drive transfer.

In the illustrated example the slots are aligned at one end. An end of the first slot proximal to an indent 712 in the interface structure 700 is aligned with an end of the second slot proximal to the indent 712 and an end of the third slot proximal to the indent 712. When the drive transfer elements are moved, for example by being driven, to their furthest extent towards the indent 712, each of the drive transfer elements will be aligned with the others. Where the ends of the slots, or the drive transfer elements, are aligned, they may be at the same distance as one another along a length of the interface structure.

In other examples, the length of the slots need not match the length of the linear paths. Suitably the slots are at least as long as the linear paths.

This arrangement assists in restricting fluid flow through the aperture or slot. Restricting this fluid flow assists in maintaining a sterile barrier. Thus when attached to a surgical robot arm, and/or to a surgical instrument, the interface structure can assist in maintaining the sterile barrier between the arm and the instrument.

As mentioned above, the central portion 736 of the first drive transfer element 706 comprises a protrusion to the second side 702 of the interface structure 700. As can be seen from FIG. 7a, each of the drive transfer elements comprises a central portion which comprises a protrusion to the second side 702 of the interface structure 700. In this example, the central portions of the drive transfer elements comprise recesses to the first side 701 of the interface structure 700 (visible in FIG. 7b) for engagement with the fins of the respective drive assembly interface elements.

In other examples, the central portions of the drive transfer elements can be arranged the other way round. In other words, recesses can be provided towards the second side and protrusions can be provided towards the first side. Alternatively, any combination of protrusions and recesses can be provided. This can include one drive transfer element comprising either both a protrusion towards the first side and a protrusion towards the second side, or a recess towards the first side and a recess towards the second side. The configuration adopted will suitably match that of the drive assembly interface 400 and the instrument interface 500. In other words, where a drive assembly interface element comprises a protruding fin, the central portion of the respective drive transfer element towards the first side will comprise a recess for receiving the fin. Where the drive assembly interface element comprises a recess, the central portion of the respective drive transfer element towards the first side will comprise a protrusion for engaging with the recess. Similarly, where the instrument interface element comprises a protruding fin, the central portion of the respective drive transfer element towards the second side will comprise a recess for receiving the fin. Where the instrument interface element comprises a recess, the central portion of the respective drive transfer element towards the second side will comprise a protrusion for engaging with the recess.

Suitably the drive transfer elements comprise a plastic material. Preferably the drive transfer elements are able to deform slightly so as to accommodate interfacing with the drive assembly interface elements and/or the instrument interface elements. Preferably the drive transfer elements engage with the drive assembly interface elements by an interference fit, such as a light interference fit. Suitably the drive transfer elements engage with the instrument interface elements by an interference fit, such as a light interference fit.

Generally, each drive transfer element comprises a first portion and a second portion. The central portion suitably comprises the first portion and the second portion. The first portion is engageable with the robot arm. For example, the first portion is engageable with the drive assembly interface, such as being engageable with a drive assembly interface element. The second portion is engageable with the instrument. For example, the second portion is engageable with the instrument interface, such as being engageable with an instrument interface element.

To put it another way, at least one of the first portion and the second portion can be a drive transfer element recess, or a recess in the drive transfer element. At least one of the first portion and the second portion can be a drive transfer element protrusion, or a protruding portion of the drive transfer element. Preferably, the drive transfer element comprises both a drive transfer element recess and a drive transfer element protrusion.

The drive transfer element recess is engageable with an interface protrusion, such as a protrusion on a drive assembly interface element or on an instrument interface element. The drive transfer element protrusion is engageable with an interface recess, such as a recess in a drive assembly interface element or in an instrument interface element.

Referring to the illustrated example, the first portion comprises a recess and the second portion comprises a protrusion. The protrusion of the second portion comprises a chamfer and/or rounded edge to ease engagement of the protrusion with a cup, such as a cup on an instrument interface element, into which the protrusion is receivable. In the illustrated example, as best seen from FIGS. 7a and 9 the protrusion of the second portion has a V-shape in cross-section. This aids in engaging the protrusion with the cup. The V-shape of the protrusion can accommodate misalignment between the protrusion and the cup as the instrument is attached to the interface structure. The recess of the first portion comprises a flared and/or rounded edge adjacent the opening into the recess to ease engagement with a protrusion or fin, such as a protrusion or fin on a drive assembly interface element, with which the recess is engageable.

Preferably, the first portion and the drive assembly interface element comprise cooperating surfaces which are complementary to one another. Preferably, the second portion and the instrument interface element comprise cooperating surfaces which are complementary to one another. Referring to FIG. 9, an interior of the cup of the instrument interface element is shaped to be complementary to an exterior of the protrusion on the drive transfer element, and an interior of the drive transfer element is shaped to be complementary to an exterior of the protrusion of the drive assembly interface element.

Where one of the first portion and the second portion is a recess and the other of the first portion and the second portion is a protrusion, the recess 901 can communicate with a cavity 902 in the protrusion 903, as can be seen from FIG. 9. A fin 930 receivable into the recess can be receivable into the cavity through the recess. This can provide a more stable engagement between the drive assembly and the interface structure, between the interface structure and the instrument, and/or between the drive assembly and the instrument.

The drive transfer element comprises an outer edge or wall 904. The outer wall 904 faces to the left in FIG. 9. The outer wall 904 faces a direction in which the drive transfer element can be driven by the drive assembly interface element. The outer wall 904 contacts, or engages with, a socket inner wall 905 of the socket or cup 502 of the instrument interface element. The socket inner wall 905 faces an opposing direction, such as an opposite direction, to that faced by the outer wall 904. In the illustrated example, the outer wall 904 and the socket inner wall 905 face in opposite directions. The drive transfer element comprises an inner edge or wall 906. The inner wall 906 faces to the right in FIG. 9. The inner wall 906 opposes a direction in which the drive transfer element can be driven by the drive assembly interface element. For example, referring to FIG. 9, the inner wall 906 is opposite to a direction in which the drive transfer element can be driven (the drive transfer element can be driven to the left, and the inner wall 906 faces to the right). The inner wall 906 contacts, or engages with, a portion of the drive assembly interface element. In the illustrated example the drive assembly interface element comprises a protrusion or fin 930 which contacts the inner wall 906 of the drive transfer element. Thus drive is transferable from the drive assembly interface element 930 to the inner wall 906 of the drive transfer element, and from the outer wall 904 of the drive transfer element to the socket inner wall 905.

The outer wall 904 and the socket inner wall 905 overlap one another in the direction in which the drive transfer element is movable, i.e. in the direction in which drive is transferrable between the drive assembly interface element and the instrument interface element. Suitably the outer wall 904 overlaps the whole of the socket inner wall 905.

Increasing, or maximising, the overlap between the outer wall 904 and the socket inner wall 905, in other words increasing the area of overlap, can reduce, or minimise, the pressure on the drive transfer element. Thus a greater overlap reduces pressure between the drive assembly interface element and the instrument interface element. Pressure could be reduced by increasing the width of the overlap. This might, however, cause the width of the interfaces to increase, all other things remaining equal. Preferably, where the width of overlap is increased, this is accommodated within the interfaces to avoid needing to increase the overall width of the interfaces.

Pressure could be reduced by increasing the height, or vertical (with respect to FIG. 9) extent, of the overlap. This might, however, cause the height of the interfaces to increase, all other things remaining equal. Preferably, where the height of overlap is increased, this is accommodated within the interfaces to avoid needing to increase the overall height of the interfaces. One way of achieving this is to provide the drive assembly interface element and instrument interface element at relative positions such that the vertical overlap is increased without affecting the overall height of the structure. Providing the cup 502 (which in the example illustrated in FIG. 9 is located on the instrument interface element, but which, as described above, could alternatively be located on the drive assembly interface element) so as to at least partially protrude within the slot, as described above, can lead to an increase in the area of overlap without necessarily causing the overall height to increase.

In a similar manner, another outer wall (for example a second outer wall) of the drive transfer element faces to the right (in FIG. 9). The second outer wall faces another direction in which the drive transfer element can be driven by the drive assembly interface element. The second outer wall contacts, or engages with, another socket inner wall (for example a second socket inner wall) of the socket 502. The second socket inner wall faces an opposing direction, such as an opposite direction, to that faced by the second outer wall. The drive transfer element comprises a second inner edge or wall. The second inner wall opposes the other direction in which the drive transfer element can be driven by the drive assembly interface element. The second inner wall contacts, or engages with, a portion of the drive assembly interface element. Thus drive is transferable from the drive assembly interface element to the second inner wall of the drive transfer element, and from the second outer wall of the drive transfer element to the second socket inner wall.

The second outer wall and the second socket inner wall overlap one another in the direction (to the right in FIG. 9) in which the drive transfer element is movable, i.e. in the direction in which drive is transferrable between the drive assembly interface element and the instrument interface element. Suitably the second outer wall overlaps the whole of the second socket inner wall.

The outer wall and the socket inner wall are, in the example illustrated in FIG. 9, parallel to one another. The second outer wall and the second socket inner wall are, in the example illustrated in FIG. 9, parallel to one another. In other examples, either or both pairs of walls need not be parallel to one another.

The inner wall and a wall of the drive assembly interface element arranged to be adjacent the inner wall are, in the example illustrated in FIG. 9, parallel to one another. The second inner wall and a wall of the drive assembly interface element arranged to be adjacent the second inner wall are, in the example illustrated in FIG. 9, parallel to one another. In other examples, either or both of these pairs of walls need not be parallel to one another.

The overlap of the outer wall and the socket inner wall (and/or of the second outer wall and the second socket inner wall) permits drive to be transferred by a compressive force, such as a substantially compressive force. Where the pairs of walls are parallel to one another, and the walls are transverse to the direction in which drive is transferable, the force will be a compressive force. An increasing deviation from this arrangement will result in a reduction in the compressive component of the force, and an increase in other components of the force, for example bending or shear components.

In other examples, drive need not be transferred via overlapping portions of the walls. Drive can be transferable, at least in part, via a portion of the drive transfer element which does not overlap with the drive assembly interface element in the direction of drive transfer. For example, drive can be transferable via the V-shaped portion of the drive transfer element (or, more generally, via a rounded and/or chamfered portion of the drive transfer element). This arrangement may provide a greater positional tolerance between the drive transfer element and the instrument interface element whilst still being able to transfer drive. An interference fit, though preferable also in this arrangement, would again not be necessary. In such an arrangement, a force which is vertical in the orientation of FIG. 9 is likely to be advantageously provided to assist in keeping the drive assembly interface elements and the instrument interface elements in an engaged configuration as drive is transferred.

The size or width of an opening (in a direction in which drive is transferrable) of the drive transfer element recess 901 is larger than that of the cavity 902. Referring to FIG. 9, both the recess and the cavity are provided centrally in the drive transfer element in a left-right direction, i.e. one in which the drive transfer element is movable. Since the recess has a larger width than the cavity, the inner walls of the recess are not co-planar with the inner walls of the cavity. The inner walls of the recess are outwardly offset from the inner walls of the cavity.

This offsetting of the internal walls of the drive transfer element recess and the cavity can permit the interface protrusion to be engaged within the cavity without being engaged by the walls of the drive transfer element recess. This arrangement can assist in providing drive transfer through the walls of the cavity. In turn, this can assist in reducing the bending moment on the drive transfer element when being driven. This arrangement can reduce the components of the drive transfer force other than the compressive component.

Suitably the drive transfer element protrusion comprises a chamfer or rounded portion at or towards its distal end to ease engagement of the drive transfer element protrusion with the interface recess. Suitably the drive transfer element recess comprises a chamfer or rounded portion at its opening to ease engagement of the interface protrusion with the drive transfer element recess. Referring to FIG. 9, the offsetting of the walls of the recess from the walls of the cavity provide a lip between the recess and the cavity. Suitably the lip is angled or rounded to ease engagement of the interface protrusion with the cavity through the drive transfer element recess and past the lip.

The drive assembly interface element comprises an elongate protruding portion and a drive assembly interface element body 920. The elongate protruding portion is receivable into the drive transfer element recess 901. A strengthening and/or stiffening portion 921 is provided on the drive assembly interface element proximal to the drive assembly interface element body 920. Referring to FIG. 9, the strengthening or stiffening portion is a buttress portion. In other examples the strengthening or stiffening portion is a strut, or other abutment or fillet, or a gusset. The strengthening or stiffening portion can be any combination of these. The strengthening or stiffening portion can be made of a stronger and/or stiffer material than the drive assembly interface element body, for example titanium. Preferably the strengthening or stiffening portion 921 is provided on the sides of the drive assembly interface element towards and/or away from a direction in which the drive assembly interface element is movable. The strengthening or stiffening portion, such as the buttress portion, suitably resists bending of the drive assembly interface element, for example as the drive assembly interface element is moved or driven. Suitably the drive assembly interface element is strong enough and/or stiff enough to withstand a force of at least 80N without breaking. Suitably the drive assembly interface element is strong enough and/or stiff enough to withstand a force of at least 130N without breaking. Suitably the drive assembly interface element can resist a force of at least 80N, and preferably of at least 130N.

The interface structure comprises a first fastener 740 for retaining the interface structure 700 on the robot arm when the interface structure is mounted, or attached, to the robot arm. The drive assembly interface 400 comprises a retention lip 440. The first fastener 740 is engageable with the retention lip 440. The first fastener 740 comprises a ridge 742. During attachment of the interface structure 700 to the drive assembly 400, the ridge 742 passes over the retention lip 440. The first fastener is resilient to permit flexing so that the ridge 742 can pass over the retention lip 440. Once the first fastener has passed the retention lip, a flat portion 743 at the rear of the first fastener (in the direction of attachment) abuts a front portion of the retention lip (again, in the direction of attachment) and resists movement of the interface structure 700 in a direction away from the robot arm along the longitudinal axis 413 of the distal end 404 of the arm. In this way, the interface structure 700 is retained in position attached to the drive assembly interface 400. To remove the interface structure 700 from the robot arm, the first fastener can be released. The first fastener 740 is releasable by resiliently deforming the first fastener so as to lift the ridge 742 over the retention lip 440. In the example illustrated in FIGS. 7a and 7b, the first fastener comprises a tab 744. The tab 744 permits a user to lift the first fastener so as to disengage the ridge 742 from the retention lip 440. The tab 744 need not be provided in all examples. The engagement of the first fastener with the retention lip can provide tactile feedback that the interface structure is correctly or properly attached to the robot arm.

Additional retention features are provided on an edge 750 of the interface structure 700 in the illustrated example. As illustrated in FIG. 7b, one edge 750 of the interface structure comprises on an internal face thereof two lugs 751, 752. The lugs 751, 752 protrude inwardly from the internal face of the edge 750 of the interface structure 700. Cooperating retention features are provided on an outer edge of the drive assembly interface 400. Two passages 451, 452 are provided on the outer edge of the drive assembly interface 400 which communicate with a retention channel 453. In the illustrated example a common retention channel communicates with both passages, but this need not be the case. In alternatives, each passage can communicate with a respective retention channel. The passages 451, 452 and the retention channel 453 are formed as recesses in the outer edge of the drive assembly interface 400.

As the interface structure 700 is mounted to the drive assembly interface 400, the lugs 751, 752 will pass through the passages 451, 452 and into the retention channel 453. The interface structure 700 can be moved along the longitudinal axis 413 of the distal end of the arm 404. The retention channel 453 is parallel to the longitudinal axis 413 of the distal end of the arm. The movement of the interface structure in this direction (i.e. parallel to the longitudinal axis 413) moves the lugs along the retention channel 453 away from the openings to the passages 451, 452. At the same time, the first fastener 740 is moved to engage with the retention lip 440. When the lugs 751, 752 are moved away from the openings to the passages 451, 452, the interface structure will be restricted to move along the longitudinal axis 413 of the arm 404. The lugs 751, 752 will abut an upper edge 454 of the retention channel 453 to restrict movement of the interface structure 700 away from the drive assembly interface 400 in a direction transverse to the longitudinal axis 413. In other words, the engagement of the lugs in the retention channel will prevent or restrict the interface structure from being lifted off the drive assembly.

As can be seen from FIG. 7b, in this example the lugs 751, 752 comprise an upright portion 753, 754. As the interface structure is moved along the longitudinal axis 413 of the distal end of the arm 404 so as to engage the lugs in the retention channel 453, the front face of the upright portions 753, 754 will move into abutment with faces 455, 456 adjacent the passages 451, 452. This abutment between the upright portions 753, 754 and the faces 455, 456 serves to limit the movement of the interface structure, and provides tactile feedback that the limit of travel has been reached. The upright portions 753, 754 need not be provided in every example.

This combination of retention features of the interface structure 700, i.e. the first fastener 740 and the lugs 751, 752, restrict the removal of the interface structure 700 from the robot arm.

The interface structure is suitably configured to fully engage with the drive assembly interface whilst being moved a distance along the longitudinal axis 413 of the arm that is the same as or less than the distance of travel of a drive transfer element permitted by the shortest slot (i.e. in the example above, a distance of up to 6 mm). The drive transfer elements of the interface structure engage with the drive assembly interface elements as the interface structure is mounted on the drive assembly. As the main body of the interface structure is moved relative to the drive assembly so as to engage the retention features of the interface structure with those of the drive assembly, the drive transfer elements are restricted in movement by virtue of being engaged with the drive assembly elements.

Thus as the interface structure is moved into engagement, the drive transfer elements will move relative to the main body. Restricting the possible extent of travel of the main body relative to the drive assembly interface to the same as or less than the extent of travel of the drive transfer element with the shortest travel can prevent that drive transfer element from being urged past its extent of travel. This can reduce potential damage to the interface structure, and assist in maintaining the sterile barrier.

In one example, prior to attaching the interface structure to the drive assembly interface, the drive assembly interface elements are driven to a desired position, such as an interfacing position. Suitably the interfacing position, or the desired position, is for engaging the drive assembly interface elements with respective instrument interface elements. This desired position is suitably with the drive assembly interface elements at one end of their respective travel, for instance towards the end of the drive assembly interface away from the proximal end of the robot arm. The interface structure can be arranged so that the drive transfer elements are correspondingly at cooperating positions within their respective travel, for instance with one of the drive transfer elements (suitably the drive transfer element with the shortest extent of travel) being at one end of its respective travel. In this way, the engagement of the drive transfer elements with the drive assembly interface elements is reliably effected. This method of engagement can be done without needing to drive or otherwise move the drive transfer elements and/or the drive assembly interface elements back and forth to effect engagement.

Engaging the interface structure with the drive assembly in this way can mean that the main body of the interface structure is then able to move relative to the drive assembly interface by up to the full travel of the drive transfer element with the shortest travel.

To determine whether the drive assembly interface elements are in, or have been driven to, the desired position, in one example the drive assembly comprises a sensor. Preferably the drive assembly comprises a plurality of sensors, a respective one for each drive assembly interface element. The sensor is configured to sense the position of the respective drive assembly interface element. The sensor senses, or determines, when that drive assembly interface element passes a threshold position, such as a pre-determined or known position along the extent of travel of that drive assembly interface element. Suitably the sensor comprises at least one of a magnetic sensor, such as a Hall sensor, a light sensor, a capacitive sensor, an inductive sensor, an acoustic sensor, and a microswitch. Any suitable position-determining sensor can be used. The sensor can be a proximity sensor. The sensor can be a position sensor associated with the drive assembly interface element.

The sensor, in the example schematically illustrated in FIG. 9, comprises two parts. A first part 912 of the sensor is provided in a body of the drive assembly. A second part 913 of the sensor is provided on the drive assembly interface element. As the drive assembly interface element is moved, the first part 912 moves relative to the second part 913. The first part 912 and the second part 913 are configured to interact with one another. In one example the first part 912 comprises a magnetic sensor and the second part 913 comprises a magnet. The magnetic sensor is configured to sense the magnet. The magnetic sensor is configured to output a first signal when the magnet is proximal to the magnetic sensor and a second signal when the magnet is distal from the magnetic sensor. Suitably the magnetic sensor is configured, or calibrated, so that the output changes from the second signal to the first signal when the magnet, and hence the drive assembly interface element, is less than a predetermined distance from the magnetic sensor. Thus when the magnetic sensor outputs the first signal, it can be determined that the drive assembly interface element is adjacent the magnetic sensor. The first part 912 of the sensor is located in the drive assembly so that the drive assembly interface element is adjacent the first part 912 of the sensor when it is in the desired position.

The drive assembly comprises a communication unit 914 for communicating with the control unit 309. The communication unit can be a wired and/or a wireless unit, and/or can couple the sensor, for example the first part 912 of the sensor, to the control unit 309 via a communication bus. Instead of or as well as the sensor determining the position of the drive assembly interface element and/or determining whether it is in its interfacing position, the processor is configured to receive signals, such as the first signal and the second signal, from the sensor and in dependence on the received signals to determine the position of the drive assembly interface element and/or to determine whether it is in its interfacing position. The processor can make such determinations in dependence on one or more of an algorithm and a reference table (such as a look-up table), which may be in a local memory 311 or remote memory.

Suitably where the sensor comprises a passive and an active part, the second part 913 comprises the passive part, such as the magnet, and the first part 912 comprises the active part, such as the magnetic sensor. The first part 912 can more easily be connected, for example by wires, to a power source and/or to the communication unit 914.

In some examples there is some play or tolerance in the location or position of the drive transfer elements. The play or tolerance may be provided by a small flexibility or deformation in the material of the drive transfer elements. There might be some play or tolerance in the location of the drive transfer elements in a direction along the length of the main body, and/or transverse to this direction. There may be some play or tolerance in the location of the drive transfer elements perpendicular to the main body. This play or tolerance is suitably small compared to the extent of movement of the drive transfer elements, for example to maintain positional determinability of the drive transfer elements. The play or tolerance can be less than 1 mm, for example less than 0.5 mm or preferably less than 0.25 mm.

The play or tolerance can, in one example, be provided by the distance between the channels to either side of an aperture in the main body of the interface structure being slightly greater than the width of the extending portion that is arranged to slide within the channels. The play or tolerance can, in one example, be provided by the height of a channel to one side of an aperture in the main body of the interface structure being slightly greater than a height or thickness or the extending portion that is arrange to slide within the channel. As an example, where the distance between the channels and/or the height of the channel or channels exceeds the respective width and/or thickness of the extending portion by 0.2 mm, there is a play or tolerance of 0.2 mm provided. Other values for this play or tolerance are possible.

As described above, there are provided two lugs on one side of the interface structure. Similarly, two lugs can be provided on the other side of the interface structure, as illustrated in FIG. 7b. Correspondingly the outer edge of the other side of the drive assembly interface can be provided with passages and a retention channel for receiving the lugs. In other examples a differing number of lugs can be provided on each inner side of the interface structure 700. The numbers of lugs on each side need not be the same. Preferably there is at least one lug on each side of the interface structure, though in some examples a lug need only be provided on one side of the interface structure. Providing lugs on both sides can assist in retaining the interface structure on the arm. Such a retention can be more stable and/or effective where at least one lug is provided on each side of the interface structure.

Suitably the number of passages on the outer edges of the drive assembly interface 400 correspond to the number of lugs on the inner edges of the interface structure, though this need not be the case. The number of passages on the outer edges of the drive assembly interface 400 is suitably at least the same as the number of lugs on the corresponding side of the interface structure.

As mentioned above, the retention channel can be common to all passages. In other examples a retention channel can communicate with fewer than the total number of passages on the respective side of the drive assembly interface. Each retention channel can communicate with one or more passage.

In some examples, the passages and/or the retention channels can comprise raised portions over which the lugs pass as the interface structure is attached to the robot arm. The raised portions may comprise detents. Such raised portions can provide tactile feedback that the interface structure is properly or correctly attached. The raised portions can provide additional resistance to inadvertent removal of the interface structure from the robot arm.

With the arrangement described above, the interface structure 700 is arranged to be mounted to the drive assembly interface 400 by placing it onto the drive assembly interface and then sliding it towards the robot arm (i.e. generally towards the right in the orientation of FIG. 4).

The interface structure 700 comprises a front face 760. The interface structure comprises an indent 712 towards the front face. The front face is shaped to accommodate the indent. Similarly, the drive assembly interface 400 comprises a corresponding indent 412. The drive assembly interface comprises a front face 460. As the interface structure is attached to the drive assembly interface, the indent 712 of the interface structure will at least partially pass into the indent 412 of the drive assembly interface. As the interface structure is slid along the longitudinal axis 413 of the distal end of the arm, the inner side of the front face 760 of the interface structure will abut the front face 460 of the drive assembly interface. This can restrict the interface structure from being slid too far, and can help ensure that it is correctly or properly mounted to the drive assembly interface. The indent 712 in the interface structure can act, for example together with the indent 412 of the drive assembly, as an alignment feature to assist in the alignment of the interface structure and the drive assembly.

The indent 712 in the interface structure 700 can permit a more compact arrangement. The indent is shaped and configured, or sized, to receive the shaft 501 of the instrument when the instrument is attached to the interface structure. More particularly, the indent is shaped and configured, or sized, to receive a shaft attachment 610 located at the proximal end of the shaft 501 to the instrument interface 500. The provision of the indent 712, and the corresponding indent 412 in the drive assembly interface 400 permits the instrument to be mounted to the robot arm with the longitudinal axis 512 of the instrument shaft 501 closer to the longitudinal axis 413 of the distal end of the robot arm 404. Preferably the instrument is mountable to the robot arm so that the longitudinal axis 512 of the instrument shaft 501 is collinear with the longitudinal axis 413 of the distal end of the robot arm 404.

Another feature which can permit a more compact arrangement is the arrangement of the drive transfer elements on different planes. Referring again to FIG. 7*a*, the second drive transfer element 707 is movable along a plane lower (in the perspective of the figure) than that in which the first and third drive transfer elements 706, 708 are movable. This offsetting of the drive transfer elements of the interface structure 700 permits a corresponding offsetting of the drive assembly interface elements and the instrument interface elements. Thus the drive assembly interface 400 and the instrument interface 500 can be configured to be more compact in a direction lateral to the direction in which the drive interface elements are movable when the interface structure is attached to the robot arm and the instrument. In other words, locating the central drive transfer element off-plane with respect to the outer drive transfer elements (in either direction) can permit the outer drive transfer elements (for example the axes of movement of the outer drive transfer elements) to be located closer together. This can result in a more compact arrangement.

The provision of the second, central, drive transfer element on a lower plane also assists in reducing the bending moment as the drive transfer element is driven, by bringing its axis of movement closer towards the axis of movement of the corresponding drive assembly interface element.

The retention features of the interface structure 700, for example at least one of the first fastener and the lug, are shaped and/or configured such that when the surgical instrument is detached from the surgical robot arm, the interface structure is retained on the surgical robot arm. The interface structure can be engageable with the instrument interface by a second fastener (not shown). The force required to disengage the second fastener is less than the force required to disengage the first fastener and/or the lugs. The interface structure is more securely attached to the surgical robot arm than to the surgical instrument. Thus, the interface structure and the drape to which it is incorporated, remain attached to the surgical robot arm during instrument exchange. This is important in order to reduce the time taken to change instruments, since the interface structure does not need to be re-attached to the robot arm following detachment of an instrument. It is also important in order to reduce the likelihood of the drape tearing when changing instruments, which would cause the sterile operating environment to become contaminated with the non-sterile environment on the robot arm side of the drape.

The main body 704 of the interface structure 700 is rigid in the illustrated example. In other examples it need not be rigid. At least a portion of the main body 704 can be of a resilient and/or deformable material. At least a portion of the main body can be flexible. A portion of the main body can be a flexible material such as a fabric. A portion of the main body can be unconstrained. The resilience, flexibility and/or unconstrained nature of the portion of the main body can permit and/or accommodate relative movement between the drive transfer elements.

Suitably a portion of the main body between the apertures is resilient and/or deformable, for example flexible. Suitably the main body can be formed in whole or in part of a resilient and/or deformable material. The resilient and/or deformable material can comprise one or more of silicone, latex, vinyl, butyl, nitrile, neoprene, and a polymer. The resilient and/or deformable material suitably comprises a material with a low modulus and low hysteresis. The resilient and/or deformable material suitably comprises a material with a good strain to failure.

In another example, illustrated schematically in FIG. 10, the interface structure comprises one or more movable portions 1010. The movable portion is flexible and/or elastic. For example, the movable portion is a material such as a fabric. Preferably the material is water-resistant to assist in providing the sterile barrier between the robot arm and the instrument. The material can be constructed of a plastic sheet, for example made of polyester, polypropylene, polyethylene or polytetrafluoroethylene (PTFE). The movable portion 1010 reduces the likelihood that the material of the interface structure ruckles and/or controls the extent to which the material of the interface structure ruckles, though it need not do this in all examples. The movable portion is arranged to control the manner in which material of the interface structure moves as the drive transfer elements 1001, 1002, 1003 move. This can permit control of, and/or reaction to, the tension within the material of the interface structure.

The first portion and/or the second portion is attached to the movable portion. In other examples, the first portion can be attached to one movable portion. The second portion can be attached to another movable portion. The flexible and/or elastic nature of the movable portion can assist in accommodating movement of the first and/or the second portions relative to the main body.

In the illustrated example, two reels 1011, 1012 are provided. Each reel is configured to hold and retain an amount of material. Material can be rolled onto one or both reels to take up slack in the material between the reels. Material can be rolled off one or both reels to relieve tension in the material between the reels. Material can be rolled onto or off the reels to accommodate movement of the drive transfer elements.

Figure 10A:
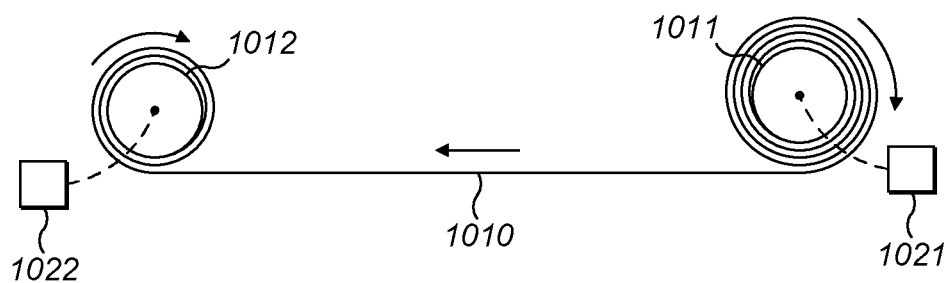
FIG. 10a schematically illustrates a side view of an alternative interface structure.

Referring to FIG. 10*a*, the material between the reels moves to the left. This is, for example, because the drive transfer element attached to that material (not shown) is driven to the left by the drive assembly. As a drive assembly interface element to which that drive transfer element is engaged moves to the left, so will the material held by the drive transfer element. The right-hand reel 1011 will rotate clockwise, as indicted by the arrow, to feed material from the right-hand reel 1011. This means that material between the drive transfer element and the right-hand reel 1011 is not exposed to a high tension that might otherwise cause a rupture in the material, and/or disrupt operation of the interface structure and/or the instrument interface. The left-hand reel 1012 can rotate anti-clockwise, as indicated by the arrow, to roll material onto the left-hand reel 1012. This means that material between the drive transfer element and the left-hand reel 1012 does not become loose. Similarly, if the drive transfer element moves to the right, material will be fed from the left-hand reel 1012. Material can be taken up by the right-hand reel 1011. Either or both of the left-hand reel 1012 and the right-hand reel 1011 need not take up slack in the material. However, maintaining the material taut can assist in covering the aperture and in maintaining the sterile barrier.

Figure 10B:
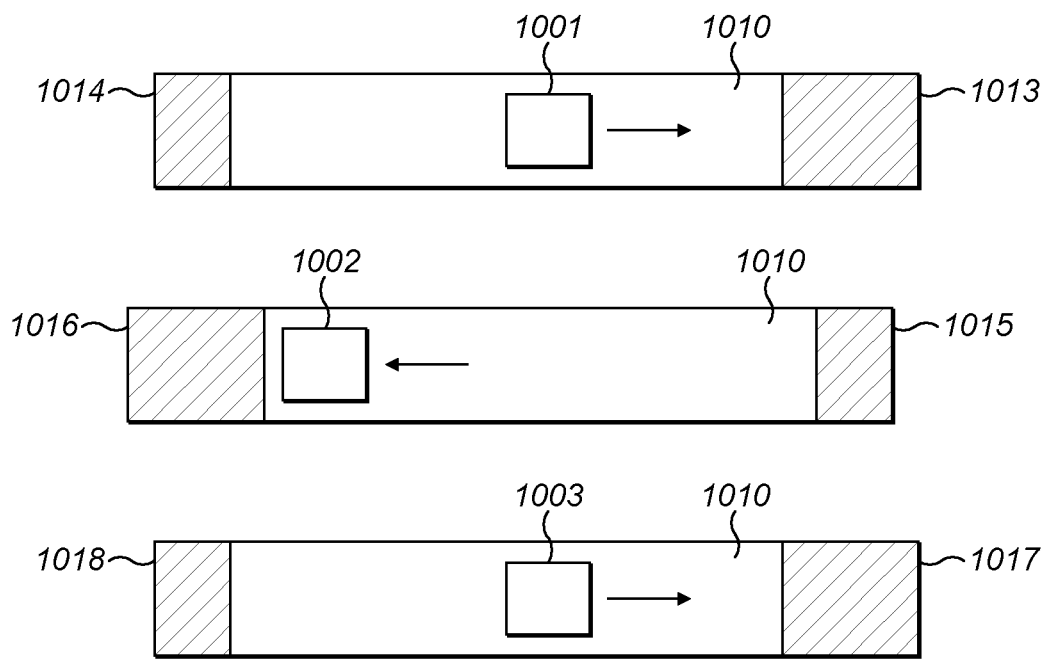

Referring now to FIG. 10*b*, where three drive transfer elements 1001, 1002, 1003 are provided adjacent one another, three pairs of reels are provided. This permits each of the three drive transfer elements to move independently of one another without such independent movement causing tension to increase in the material of the interface structure. For example, the provision of a pair of reels for each drive transfer element can reduce the extent to which the material between the reels, i.e. the movable portion, is exposed to tension, shear forces and/or rupture. This may be compared to an arrangement in which a single pair of reels is provided for a plurality of drive transfer elements, and the positioning of the material is based, for example, on an average such as a weighted average of the positions of the plurality of drive transfer elements.

In the illustrated example, an uppermost (in the orientation of FIG. 10*b*) drive transfer element 1001 is moved to the right (as indicated by the arrow), a middle drive transfer element 1002 is moved to the left (as indicated by the arrow) and a lower drive transfer element 1003 is moved to the right (as indicated by the arrow). A first right-hand reel 1013, that of the uppermost section, takes up material of the movable portion and so has a greater reel diameter. A first left-hand reel 1014, that of the uppermost section, feeds material of the movable portion from the reel and so has a smaller reel diameter. A second right-hand reel 1015, that of the middle section, feeds material of the movable portion from the reel and so has a smaller reel diameter. A second left-hand reel 1016, that of the middle section, takes up material of the movable portion and so has a greater reel diameter. A third right-hand reel 1017, that of the lower section, takes up material of the movable portion and so has a greater reel diameter. A third left-hand reel 1018, that of the lower section, feeds material of the movable portion from the reel and so has a smaller reel diameter.

It will be understood that where the number and/or arrangement of the drive transfer elements differs from the illustrated example, the number and/or arrangement of the pairs of reels can similarly differ.

Provision of a reel can assist in reducing the length of the interface structure compared to provision of rigid drive transfer elements. Provision of a reel can ensure that the sterile barrier is maintained whilst reducing the length of the interface structure needed. This is because the reel can take up material that might otherwise have projected past (overlapped) the end of the slot when the central portion is adjacent that end of the slot.

Material of the interface structure, such as the movable portion, can be taken up and/or fed from a reel by driving the respective reel about its axis. Material of the interface structure can be taken up and/or fed from a reel by resiliently biasing the respective reel about its axis. In one example each reel is resiliently biased and is also driven.

Resiliently biasing a reel can assist in keeping tension within the material of the interface structure consistent. When tension is lowered (by, for example, a drive transfer element moving towards the relevant reel), the biasing of the reel will cause the reel to rotate so as to take up material. When tension is increased (by, for example, a drive transfer element moving away from the relevant reel), the biasing of the reel will permit the reel to rotate to as to feed material from the reel.

The resilience of the resilient biasing can be determined to provide for a desired tension or range of tension in the material of the interface structure. The resilient biasing is, in one example, provided by a spring coupled to the respective reel.

Driving of the reels can be accomplished by coupling a motor, such as an electric motor, to each reel. Driving the reels can permit tension to be released and/or slack taken up at a desired speed. For example, driving the reels can permit tension to be released and/or slack taken up at a higher speed than might occur with resilient biasing. Driving the reels can permit tension to be controlled more accurately than by relying on resilient biasing, or on resilient biasing alone.

In one example, one of a pair of reels is coupled to a motor for driving that reel, and the other of the pair of reels is resiliently biased. The resilient biasing adapts to the tension in the material whilst the motor is driven so as to achieve a desired tension. This arrangement permits control of the tension in the material of the interface structure.

A first tension sensor 1021 (shown schematically in FIG. 10*a*) is coupled to the right-hand reel 1011, 1013, 1015, 1017. The first tension sensor is configured to sense tension in the material between the drive transfer element and the right-hand reel. The first tension sensor is suitably coupled to a rotational axis of the right-hand reel. A second tension sensor 1022 (shown schematically in FIG. 10*a*) is coupled to the left-hand reel 1012, 1014, 1016, 1018. The second tension sensor is configured to sense tension in the material between the drive transfer element and the left-hand reel. The second tension sensor is suitably coupled to a rotational axis of the left-hand reel. Tension sensed by either or both of the first tension sensor and the second tension sensor is used to determine how to drive either or both of the right-hand reel and the left-hand reel. In other words, either or both of the right-hand reel and the left-hand reel is controlled in dependence on tension sensed by either or both of the first tension sensor and the second tension sensor.

The provision of the first tension sensor and the second tension sensor can permit a comparison of the tension sensed by each of the first and second tension sensors. This comparison can be used to detect rupture or other damage in the material. For example, if the tension sensed at both of a pair of reels reduces as a drive transfer element moves, it can be determined that the material between the reels has ruptured.

In some examples, only one tension sensor need be provided for each of a pair of reels.

In an alternative configuration of the interface structure, the aperture in the main body can be a single aperture. In this configuration where a single drive transfer element is provided, it can engage with the main body of the interface structure as described above. Where two or more drive transfer elements are provided within a single aperture of the main body, the adjacent edges of the drive transfer elements can be provided with tongue and groove features to enable the drive transfer elements to engage with one another. This can assist in restricting fluid flow paths between the drive transfer elements. It can also therefore assist in maintaining the sterile barrier.

Taking as an example a configuration in which three drive transfer elements are provided, with the first drive transfer element being provided to one side, the third drive transfer element being provided to the other side, and the second drive transfer element being provided between the first and the third drive transfer elements, tongue and groove type engagements can be provided between the first and the second drive transfer elements and between the second and the third drive transfer elements. The first and third drive transfer elements can engage with the main body of the interface structure as described above. In this configuration, the first drive transfer element can comprise (on its side adjacent the second drive transfer element) one of a first tongue and a first groove. The second drive transfer element can comprise (on its side adjacent the first drive transfer element) the other of the first tongue and the first groove. The first tongue is engageable with the first groove. The second drive transfer element can comprise (on its side adjacent the third drive transfer element) one of a second tongue and a second groove. The third drive transfer element can comprise (on its side adjacent the second drive transfer element) the other of the second tongue and the second groove. The second tongue is engageable with the second groove. This arrangement can permit the first drive transfer element to slide along the second drive transfer element and the second drive transfer element to slide along the third drive transfer element. This approach thus allows relative movement between adjacent drive transfer elements whilst still restricting fluid flow paths between the drive transfer elements.

Figure 11A:
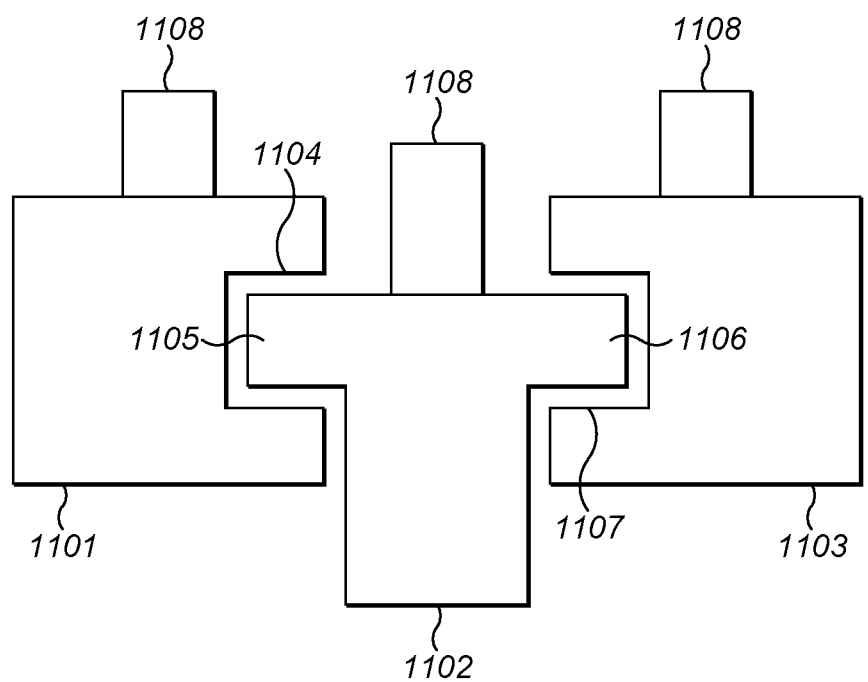
FIG. 11 schematically shows drive transfer elements of an alternative interface structure.
Figure 11B:
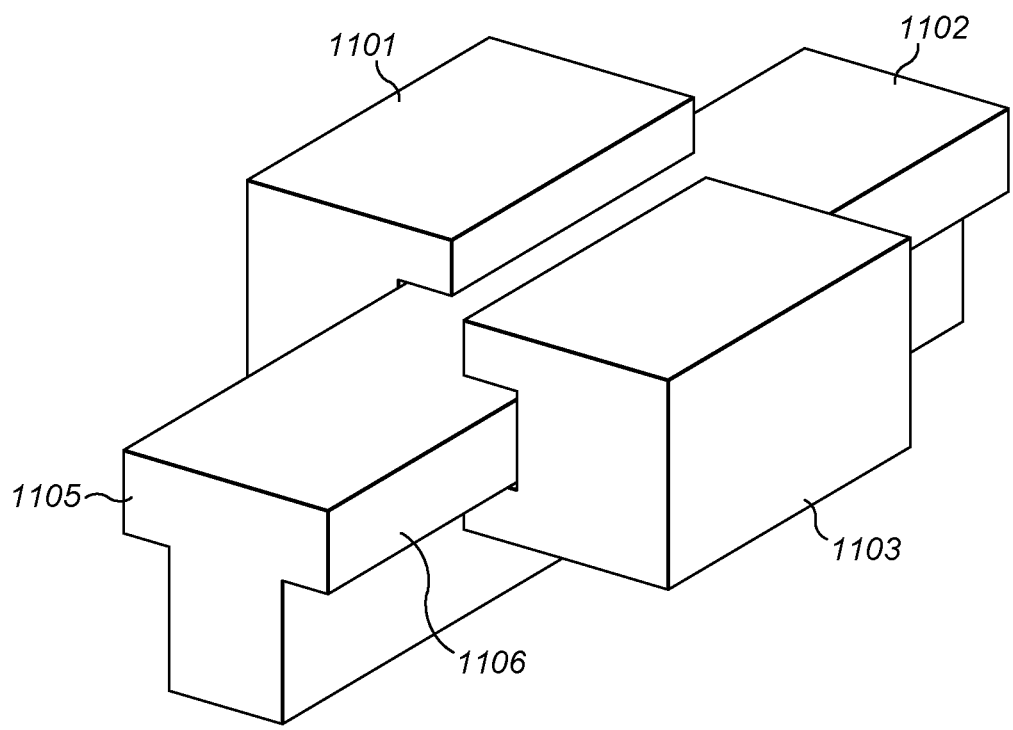

An example of such an arrangement is shown in FIG. 11. FIG. 11a schematically illustrates an end view of three drive transfer elements. FIG. 11b schematically illustrates a perspective view of the three drive transfer elements of FIG. 11a. The first drive transfer element 1101 comprises an engagement feature such as a lip (not shown) to engage with an edge of the aperture as described above. The first drive transfer element 1101 comprises the first groove 1104 on the side adjacent the second drive transfer element 1102. The second drive transfer element comprise the first tongue 1105 on the side adjacent the first drive transfer element 1101. The first tongue is engageable with the first groove so as to engage the first drive transfer element with the second drive transfer element. The second drive transfer element 1102 comprises the second tongue 1106 on the side adjacent the third drive transfer element 1103. The third drive transfer element comprises the second groove 1107 on the side adjacent the second drive transfer element. The second tongue is engageable with the second groove so as to engage the second drive transfer element with the third drive transfer element. The other side of the third drive transfer element 1103 comprises an engagement feature such as a lip (not shown) to engage with an edge of the aperture as described above. Protrusions 1108 are also schematically shown (these have been omitted from FIG. 11b for clarity). The protrusions are for engaging with recesses as described above. Recesses could instead be provided. Any combination of protrusions and recesses could be provided.

The outer boundary of the interface structure terminates in a sterile drape (not shown). The sterile drape shrouds the surgical robot arm. The inner boundary of the interface structure may terminate in a sterile membrane (not shown) which extends over the hollow interior to isolate the sterile environment from the non-sterile drive assembly.

The interface structure may be packaged with the drape, for example in a flat configuration.

Suitably, the interface structure 700 is fastened to the drive assembly as the robot arm is being shrouded in the sterile drape as part of the set-up procedure prior to the operation beginning. An instrument is subsequently fastened to the interface structure 700. At some point during the operation, the instrument is exchanged for another instrument. A different instrument can then be attached to the interface structure. Providing the interface structure, and retaining the interface structure on the robot arm when removing an instrument means that instruments can be quickly and easily detached from and attached to the robot arm during an operation without exposing the patient to a non-sterile environment.

The instrument could be used for non-surgical purposes. For example, it could be used in a cosmetic procedure. The interface structure may be used for non-surgical purposes. The barrier provided by the interface structure can be a barrier to fluid flow and/or a barrier to particulate matter, for example particulate matter entrained in a flow of fluid such as air.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A drive transfer element for transferring drive between a surgical robot arm and a surgical instrument, the drive transfer element comprising:
   a drive transfer element recess being releasably engageable with an interface protrusion; and
   a drive transfer element protrusion being releasably engageable with an interface recess;
   the drive transfer element protrusion comprising a cavity in communication with the drive transfer element recess so as to enable the interface protrusion engageable with the drive transfer element recess to project into the cavity,
   wherein the drive transfer element is arranged for movement along a linear path and wherein the drive transfer element comprises a central portion which comprises the drive transfer element protrusion and the drive transfer element recess, and an extending portion which extends from the central portion, the drive transfer element recess comprising a first inner wall extending from a first side of the extending portion and the drive transfer element protrusion comprising a first outer wall extending from a second side of the extending portion, the drive transfer element permitting the interface protrusion engageable therewith to project from the first side through to the second side.

2. A drive transfer element as claimed in claim 1, in which the drive transfer element is drivable in a first direction to effect drive transfer, and the drive transfer element protrusion comprises the first outer wall facing the first direction for contacting a portion of the interface recess and the cavity comprises the first inner wall facing a second direction for contacting a portion of the interface protrusion.

3. A drive transfer element as claimed in claim 2, in which the first outer wall and the first inner wall overlap one another in the first direction.

4. A drive transfer element as claimed in claim 2, in which the second direction is opposite to the first direction.

5. A drive transfer element as claimed in claim 2, in which the drive transfer element is drivable in a third direction to effect drive transfer and the drive transfer element protrusion comprises a second outer wall facing the third direction for contacting a portion of the interface recess and the cavity comprises a second inner wall facing a fourth direction for contacting a portion of the interface protrusion.

6. A drive transfer element as claimed in claim 5, in which the second outer wall and the second inner wall overlap one another in the third direction.

7. A drive transfer element as claimed in claim 5, in which the fourth direction is opposite to the third direction.

8. A drive transfer element as claimed in claim 5, in which the third direction is opposite to the first direction.

9. A drive transfer element as claimed in claim 1, in which the drive transfer element recess has a larger width than the cavity.

10. A drive transfer element as claimed in claim 5, in which a first wall of the drive transfer element recess disposed towards the first direction is offset from the first inner wall, and a second wall of the drive transfer element recess disposed towards the third direction is offset from the second inner wall.

11. An interface structure for detachably interfacing a surgical robot arm to a surgical instrument, the interface structure comprising:

a main body; and a drive transfer element as claimed in claim 1, the drive transfer element being movable relative to the main body so as to enable transfer of drive between the surgical robot arm and the surgical instrument.

12. An interface structure as claimed in claim 11, in which the main body comprises an aperture within which the drive transfer element is movable.

13. An interface structure as claimed in claim 12, in which the main body comprises a retention feature for retaining the drive transfer element so that the drive transfer element is movable within the aperture.

14. A surgical robot arm comprising:

a drive assembly towards a distal end of the arm which is engageable with a surgical instrument having an articulation for articulating an end effector, the drive assembly comprising a drive assembly interface element; and an interface structure as claimed in claim 11;

the drive assembly interface element being engageable with the drive transfer element so as to transfer drive between the robot arm and the instrument.

15. A surgical robot arm as claimed in claim 14, in which the drive assembly interface element comprises the interface protrusion.

16. A surgical robot arm as claimed in claim 15, in which the drive assembly interface element comprises a strengthening or stiffening portion.

* * * * *